(12) United States Patent
Barth

(10) Patent No.: US 11,225,512 B2
(45) Date of Patent: Jan. 18, 2022

(54) COMPOSITIONS AND METHODS FOR CERAMIDE-ELEVATING THERAPEUTIC STRATEGIES

(71) Applicant: University of New Hampshire, Durham, NH (US)

(72) Inventor: Brian Barth, Durham, NH (US)

(73) Assignee: University of New Hampshire, Durham, NH (US)

( * ) Notice: Subject to any disclaimer, the term of this patent is extended or adjusted under 35 U.S.C. 154(b) by 0 days.

(21) Appl. No.: 15/965,383

(22) Filed: Apr. 27, 2018

(65) Prior Publication Data
US 2018/0312556 A1   Nov. 1, 2018

Related U.S. Application Data

(60) Provisional application No. 62/602,537, filed on Apr. 27, 2017.

(51) Int. Cl.
| A61K 38/18 | (2006.01) |
| C07K 14/475 | (2006.01) |
| C07K 14/495 | (2006.01) |
| A61K 31/706 | (2006.01) |
| A61K 45/06 | (2006.01) |

(52) U.S. Cl.
CPC ........ *C07K 14/475* (2013.01); *A61K 38/1841* (2013.01); *C07K 14/495* (2013.01); *A61K 31/706* (2013.01); *A61K 38/18* (2013.01); *A61K 45/06* (2013.01); *A61K 2300/00* (2013.01); *C07K 2319/00* (2013.01)

(58) Field of Classification Search
CPC .............................. A61K 38/18; C07K 14/475
See application file for complete search history.

(56) References Cited

U.S. PATENT DOCUMENTS

| 3,854,480 | A | 12/1974 | Zaffaroni |
| 4,452,775 | A | 6/1984 | Kent |
| 4,675,189 | A | 6/1987 | Kent et al. |
| 5,075,109 | A | 12/1991 | Tice et al. |
| 5,133,974 | A | 7/1992 | Paradissis et al. |
| 5,211,657 | A | 5/1993 | Yamada et al. |
| 5,407,686 | A | 4/1995 | Patel et al. |
| 5,736,152 | A | 4/1998 | Dunn |
| 2003/0069176 | A1* | 4/2003 | Marchionni ....... A61K 38/1875 514/17.7 |
| 2007/0249535 | A1* | 10/2007 | Lee ................... A61K 38/1875 514/8.8 |
| 2009/0048431 | A1* | 2/2009 | Steward ............ A61K 38/4886 530/350 |

FOREIGN PATENT DOCUMENTS

WO   1995/24929   9/1995

OTHER PUBLICATIONS

Maler et al., Molecular Psychiatry (2006) vol. 11:1113-1115.*
(Continued)

*Primary Examiner* — Xiaozhen Xie
(74) *Attorney, Agent, or Firm* — Pierce Atwood LLP

(57) ABSTRACT

The present invention is directed towards the use of Growth Differentiation Factor 1 (Gdf1) and variants thereof to modulate and regulate ceramide neutralization in cells.

15 Claims, 8 Drawing Sheets

Specification includes a Sequence Listing.

(56) References Cited

OTHER PUBLICATIONS

Barth et al., "Ceramide-Based Therapeutics for the Treatment of Cancer." Anti-Cancer Agents in Medicinal Chemistry (2011), vol. 11, No. 9, pp. 911-919.
Esposito et al., "Enhancement of soluble protein expression through the use of fusion tags." Current Opinion in Biotechnology (2006), vol. 17, Issue 4, pp. 353-358.
GenBank Accession No. 4332888.30.
GenBank Accession No. NP_001483.
Morad, S. et al. "Ceramide-orchestrated signalling in cancer cells." Nature Reviews Cancer, (2013),vol. 13, pp. 51-65.
Papaemmanuil et al., "Genomic Classification and Prognosis in Acute Myeloid Leukemia." New England Journal of Medicine (2016), 374, pp. 2209-2221.
Sawhney et al., "Bioerodible Hydrogels Based on Photopolymerized Polyethylene glycol)-co-poly( -hydroxy acid) Diacrylate Macromers." Macromolecules1993,26, 581-587.
Navada et al., "Clinical development of demethylating agents in hematology." The Journal of Clinical Investigation, vol. 124, No. 1, Jan. 2014, pp. 40-46.

* cited by examiner

Recombinant Gdf1 Downregulates Ceramide Neutralization In Vitro

SEQUENCE LISTING

<160> NUMBER OF SEQ ID NOS: 11

<210> SEQ ID NO 1
<211> LENGTH: 372
<212> TYPE: PRT
<213> ORGANISM: Homo sapiens

<400> SEQUENCE: 1

```
Met Pro Pro Pro Gln Gln Gly Pro Cys Gly His His Leu Leu Leu Leu
1               5                   10                  15

Leu Ala Leu Leu Leu Pro Ser Leu Pro Leu Thr Arg Ala Pro Val Pro
            20                  25                  30

Pro Gly Pro Ala Ala Ala Leu Leu Gln Ala Leu Gly Leu Arg Asp Glu
        35                  40                  45
```

```
Pro Gln Gly Ala Pro Arg Leu Arg Pro Val Pro Val Met Trp Arg
    50                  55                  60

Leu Phe Arg Arg Arg Asp Pro Gln Glu Thr Arg Ser Gly Ser Arg Arg
65                  70                  75                  80

Thr Ser Pro Gly Val Thr Leu Gln Pro Cys His Val Glu Glu Leu Gly
                85                  90                  95

Val Ala Gly Asn Ile Val Arg His Ile Pro Asp Arg Gly Ala Pro Thr
            100                 105                 110

Arg Ala Ser Glu Pro Ala Ser Ala Ala Gly His Cys Pro Glu Trp Thr
        115                 120                 125

Val Val Phe Asp Leu Ser Ala Val Glu Pro Ala Glu Arg Pro Ser Arg
    130                 135                 140

Ala Arg Leu Glu Leu Arg Phe Ala Ala Ala Ala Ala Ala Pro Glu
145                 150                 155                 160

Gly Gly Trp Glu Leu Ser Val Ala Gln Ala Gly Gln Gly Ala Gly Ala
                165                 170                 175

Asp Pro Gly Pro Val Leu Leu Arg Gln Leu Val Pro Ala Leu Gly Pro
            180                 185                 190

Pro Val Arg Ala Glu Leu Leu Gly Ala Ala Trp Ala Arg Asn Ala Ser
        195                 200                 205

Trp Pro Arg Ser Leu Arg Leu Ala Leu Ala Leu Arg Pro Arg Ala Pro
    210                 215                 220

Ala Ala Cys Ala Arg Leu Ala Glu Ala Ser Leu Leu Val Thr Leu
225                 230                 235                 240

Asp Pro Arg Leu Cys His Pro Leu Ala Arg Pro Arg Arg Asp Ala Glu
                245                 250                 255

Pro Val Leu Gly Gly Pro Gly Gly Ala Cys Arg Ala Arg Arg Leu
            260                 265                 270

Tyr Val Ser Phe Arg Glu Val Gly Trp His Arg Trp Val Ile Ala Pro
        275                 280                 285

Arg Gly Phe Leu Ala Asn Tyr Cys Gln Gly Gln Cys Ala Leu Pro Val
    290                 295                 300

Ala Leu Ser Gly Ser Gly Gly Pro Pro Ala Leu Asn His Ala Val Leu
305                 310                 315                 320

Arg Ala Leu Met His Ala Ala Ala Pro Gly Ala Ala Asp Leu Pro Cys
                325                 330                 335

Cys Val Pro Ala Arg Leu Ser Pro Ile Ser Val Leu Phe Phe Asp Asn
            340                 345                 350

Ser Asp Asn Val Val Leu Arg Gln Tyr Glu Asp Met Val Val Asp Glu
        355                 360                 365

Cys Gly Cys Arg
    370

<210> SEQ ID NO 2
<211> LENGTH: 119
<212> TYPE: PRT
<213> ORGANISM: Homo sapiens

<400> SEQUENCE: 2

Asp Ala Glu Pro Val Leu Gly Gly Pro Gly Gly Ala Cys Arg Ala
1               5                   10                  15

Arg Arg Leu Tyr Val Ser Phe Arg Glu Val Gly Trp His Arg Trp Val
                20                  25                  30

Ile Ala Pro Arg Gly Phe Leu Ala Asn Tyr Cys Gln Gly Gln Cys Ala
            35                  40                  45
```

Leu Pro Val Ala Leu Ser Gly Ser Gly Gly Pro Ala Leu Asn His
          50                  55                  60

Ala Val Leu Arg Ala Leu Met His Ala Ala Pro Gly Ala Ala Asp
 65                  70                  75                  80

Leu Pro Cys Cys Val Pro Ala Arg Leu Ser Pro Ile Ser Val Leu Phe
                 85                  90                  95

Phe Asp Asn Ser Asp Asn Val Val Leu Arg Gln Tyr Glu Asp Met Val
            100                 105                 110

Val Asp Glu Cys Gly Cys Arg
        115

```
<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: A 6-FAM label is attached at 5' end and is a
      single isomer derivative of fluorescein
<220> FEATURE:
<221> NAME/KEY: misc_feature
<223> OTHER INFORMATION: An Iowa Black RQ (IBRQ) quencher is attached at
      3' end of sequence
<220> FEATURE:
<221> NAME/KEY: misc_feature
<222> LOCATION: (9)..(10)
<223> OTHER INFORMATION: A ZEN quencher is between residues 9 and 10

<400> SEQUENCE: 3
tcgtcttcga cctgtcggct gtgg                                          24

<210> SEQ ID NO 4
<211> LENGTH: 19
<212> TYPE: DNA
<213> ORGANISM: Homo sapiens

<400> SEQUENCE: 4
cattgccctg agtggacag                                                19

<210> SEQ ID NO 5
<211> LENGTH: 17
<212> TYPE: DNA
<213> ORGANISM: Homo sapiens

<400> SEQUENCE: 5
gaaacgcagc tccaggc                                                  17

<210> SEQ ID NO 6
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: A 6-FAM label is attached at 5' end and is a
      single isomer derivative of fluorescein
<220> FEATURE:
<221> NAME/KEY: misc_feature
<223> OTHER INFORMATION: An Iowa Black RQ (IBRQ) quencher is attached at
      3' end of sequence
<220> FEATURE:
<221> NAME/KEY: misc_feature
<222> LOCATION: (9)..(10)
<223> OTHER INFORMATION: A ZEN quencher is between residues 9 and 10
```

<400> SEQUENCE: 6
ctttgacaac agcgacaacg tggtgc                                          26

<210> SEQ ID NO 7
<211> LENGTH: 17
<212> TYPE: DNA
<213> ORGANISM: Homo sapiens

<400> SEQUENCE: 7
cccatctccg tgctctt                                                    17

<210> SEQ ID NO 8
<211> LENGTH: 17
<212> TYPE: DNA
<213> ORGANISM: Homo sapiens

<400> SEQUENCE: 8
cactcgtcca ccaccat                                                    17

<210> SEQ ID NO 9
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: A 6-FAM label is attached at 5' end and is a
      single isomer derivative of fluorescein
<220> FEATURE:
<221> NAME/KEY: misc_feature
<223> OTHER INFORMATION: An Iowa Black RQ (IBRQ) quencher is attached at
      3' end of sequence
<220> FEATURE:
<221> NAME/KEY: misc_feature
<222> LOCATION: (9)..(10)
<223> OTHER INFORMATION: A ZEN quencher is between residues 9 and 10

<400> SEQUENCE: 9
aacattctgc tgttgctcct gatggtcatg                                      30

<210> SEQ ID NO 10
<211> LENGTH: 22
<212> TYPE: DNA
<213> ORGANISM: Mus musculus

<400> SEQUENCE: 10
gcctgacatt ccgtactact tc                                              22

<210> SEQ ID NO 11
<211> LENGTH: 19
<212> TYPE: DNA
<213> ORGANISM: Mus musculus

<400> SEQUENCE: 11
tccagttcac gcatctgac                                                  19

_COMPOSITIONS AND METHODS FOR CERAMIDE-ELEVATING THERAPEUTIC STRATEGIES_

RELATED APPLICATIONS

This application claims benefit under 35 U.S.C. § 119(e) of U.S. Provisional application Ser. No. 62/602,537 filed Apr. 27, 2017, the disclosure of which is incorporated by reference herein in its entirety.

GOVERNMENT SUPPORT

This invention was made with government support under grant number CA190674 awarded by NIH. The government has certain rights in this invention.

FIELD OF THE INVENTION

The invention relates, in part, to detecting and modulating ceramide function in cells and subjects.

BACKGROUND OF THE INVENTION

The bioactive sphingolipid ceramide regulates cell death (apoptosis), and as such, therapeutic strategies that elevate its endogenous levels can be utilized as anti-proliferatives. This is especially useful for cancer therapy, but also for other conditions that arise from over-proliferation of cells (such as inflammatory diseases including rheumatoid arthritis), or from metabolic disorders that result in accumulations of glycosphingolipids (sphingolipidosis), as well as pathogenic infections that are influenced by ceramide glycosylation at either the host or pathogen level. Prior art therapeutic approaches that elevate cellular ceramide do so by promoting endogenous ceramide biosynthesis (either via de novo or salvage biosynthetic pathways), or may deliver exogenous ceramide (typically ceramide analogs).

The major therapeutic obstacle to ceramide-elevating therapies is metabolism of ceramide to other types of sphingolipids that otherwise do not induce cell death or may even augment cellular proliferation. One of these primary metabolic outlets is to glucosylceramide, which is generated through the catalytic activity of glucosylceramide synthase (gene symbol: ugcg). Therefore, mechanisms of resistance to ceramide-elevating therapeutic approaches often involves metabolism (neutralization) of ceramide to glucosylceramide as well as other ceramide metabolites.

Prior art strategies to overcome ceramide neutralization to glucosylceramide have centered on pharmacological inhibitors of glucosylceramide synthase, or p-glycoprotein (P-GP). It has been suggested that P-GP is a lipid flippase that works in tandem with glucosylceramide synthase. This has opened up the possibility of using P-GP inhibitors. As inhibitors of ceramide neutralization, however, many of these inhibitors have failed in clinical trials due to toxicity issues. Overall, effective and efficient modification of ceramide neutralization are not available.

SUMMARY OF THE INVENTION

The present invention is directed towards the use of Growth Differentiation Factor 1 (Gdf1) and variants thereof to modulate and regulate ceramide neutralization. The present invention is directed towards the use of recombinant Gdf1 supplementation (for example, via administration of exogenous peptide), or strategies to augment endogenous production of Gdf1 (for example, via an expression vector encoding Gdf1) or supplementing other treatments (for example, supplementing hypomethylating therapy such as decitabine treatment), for the downregulation of ceramide neutralization. Although the present invention is not limited by theory, the present inventors have found that Gdf1 is effective in modulating and regulating ceramide neutralization, at least in part, by downregulating the expression of Glucosylceramide Synthase (ugcg) and Sphingomyelin Synthase 1 (sgms 1). Further, the present inventors have found that Gdf1 also induces the differentiation of hematopoietic stem cells by promoting an exit from quiescence thereby making them more susceptible to anti-cancer treatments. Therefore, Gdf1 acts to simultaneously target cancer/leukemia stem cells by promoting their differentiation and augmenting the sensitivity of these cells (and non-stem cell cancer cells) to ceramide-elevating therapeutics by downregulating ceramide neutralization by downregulating the expression of ugcg. The present invention is also directed towards the downregulation by Gdf1 of another aspect of ceramide neutralization by downregulating the expression of sphingomyelin synthase 1 (sgms 1). The present invention is still further directed towards the use of Gdf1 as an effective combinatorial agent with other ceramide-elevating therapeutics.

In addition, the present invention is directed towards the use of Gdf1 as a form of substrate reduction therapy for sphingolipidosis by preventing the metabolism of ceramide to glucosylceramide (and subsequent higher order glycosphingolipids). In a similar manner, the present invention is directed towards the use of Gdf1 as a form of substrate reduction therapy for sphingolipidosis characterized by accumulations of sphingomyelin. Finally, the present invention is directed towards the use of Gdf1 to antagonize and reduce one or more host-pathogen processes that rely on ceramide metabolism to accumulate glucosylceramide or sphingomyelin.

In one aspect, the present invention is directed towards a method of modulating ceramide neutralization in a cell, the method comprising: contacting the cell with an effective amount of a composition comprising one or more agents selected from the group consisting of exogenous Growth Differentiation Factor 1 (Gdf1) or functional variant thereof; an active fragment of the Gdf1 protein or functional variant thereof; an expression vector encoding Gdf1 or functional variant thereof; or an expression vector encoding an active fragment of Gdf1 or functional variant thereof, to modulate ceramide neutralization.

The method may comprise detecting a change in ceramide bioactivity changes in the cell as compared to essentially equivalent control cells not contacted with the composition. Changes in ceramide bioactivity may comprise one or both of changes in ceramide gene expression and ceramide enzyme activity. Detecting ceramide bioactivity may comprise detecting changes in one or both of the activity and the expression level of at least one ceramide metabolic enzyme.

The method of the present invention may further comprise detecting a change in any ceramide and ceramide metabolite levels in the essentially equivalent cells (i.e., control cells) not contacted with the composition.

The method of the present invention may further comprise that modulating ceramide neutralization comprises modulating or downregulating the ceramide neutralization.

The method of the present invention may further comprise that the cell in which ceramide neutralization is being modulated is one or more of a: malignant, neoplastic, cancer, and leukemia cell. It is also contemplated that the cell in which ceramide neutralization is being modulated is one or more of a: pre-malignant, pre-neoplastic, pre-cancerous, and pre-leukemic cell. The present invention also contemplates that the composition for modulating ceramide neutralization in the cell also causes the cell to differentiate.

The method of the present invention may further comprise administering a compound having an activity that is reduced by ceramide neutralization.

The method of the present invention may further comprise administering an effective amount of an additional agent capable of modulating at least one of Gdf1 protein expression and activity. The additional agent may be decitabine (5-aza-2'-deoxycytidine) or another hypomethylating agent.

The method of the present invention may further comprise that the agent comprises the amino acid sequence set forth herein as SEQ ID NO: 1, or its encoding nucleic acid sequence. The method of the present invention may further comprise that the amino acid sequence of the functional variant of the Gdf1 protein has at least 95%, 96%, 97%, 98%, 99% identity to the sequence set forth herein as SEQ ID NO: 1. The method of the present invention may further comprise that the amino acid sequence of the functional variant of the Gdf1 protein has 1, 2, 3, 4, 5, 6, or more sequence modifications. The method of the present invention may further comprise that the sequence modifications are conservative amino acid substitutions.

The method of the present invention may further comprise that the agent comprises the amino acid sequence set forth herein as SEQ ID NO: 2, or its encoding nucleic acid sequence. The method of the present invention may further comprise that the amino acid sequence of the functional variant of the Gdf1 protein has at least 95%, 96%, 97%, 98%, 99% identity to the sequence set forth herein as SEQ ID NO: 2. The method of the present invention may further comprise that the amino acid sequence of the functional variant of the Gdf1 protein has 1, 2, 3, 4, 5, 6, or more sequence modifications. The method of the present invention may further comprise that the sequence modifications are conservative amino acid substitutions.

The composition of the method of the present invention may further comprise that one or more of a targeting agent, a delivery agent, a vector sequence, and a detectable label. Further, the method of the present invention may further comprise that the Gdf1 protein, Gdf1 functional variant, Gdf1 fragment, and Gdf1 fragment functional variant are part of a fusion protein.

In another aspect, the present invention is directed towards a method of modulating ceramide neutralization in a subject, the method comprising: providing: i) a subject in need of modulation of ceramide neutralization and ii) a composition comprising one or more agents selected from the group consisting of an exogenous Gdf1 protein or functional variant thereof; an active fragment of the exogenous Gdf1 protein or functional variant thereof; an expression vector encoding the Gdf1 protein or functional variant thereof; or an expression vector encoding an active fragment of the Gdf1 protein or functional variant thereof; administering to the subject a therapeutic amount of the agent; detecting ceramide neutralization in the subject; comparing the detected ceramide neutralization to ceramide neutralization detected in the subject prior to administration of the composition; and optionally, administering the composition until a change in ceramide neutralization is detected. The method of the present invention may further comprise that modulating the ceramide neutralization comprises downregulating the ceramide neutralization.

The method of the present invention may further comprise administering to the subject a compound that is inhibited by ceramide neutralization.

The method of the present invention may further comprise that the means of detecting ceramide neutralization comprises determining a change in one or more of: ceramide gene expression; regulation of ceramide enzymes; ceramide levels; and ceramide metabolite levels.

The method of the present invention may further comprise administering an effective amount of an additional agent capable of modulating one or more of Gdf1 expression and activity. The additional agent may be decitabine (5-aza-2'-deoxycytidine) or other hypomethylating agent.

The method of the present invention may further comprise that the subject has or is suspected of having a malignancy, neoplasia, cancer, or leukemia. The method of the present invention may further comprise that the subject has or is suspected of having one or more of: a pre-malignant condition, a pre-neoplastic condition, a pre-cancerous condition, and a pre-leukemic condition. The pre-leukemic condition may be a myelodysplastic syndrome or a myeloproliferative neoplasia.

The method of the present invention may further comprise that administering the composition causes differentiation of one or more of a malignant cell, a neoplastic cell, a cancerous cell, a leukemic cell in the subject. The method of the present invention may further comprise that administering the composition causes differentiation of one or more of a malignant precursor cell, a neoplastic precursor cell, a cancerous precursor cell, a leukemic precursor cell, or a stem cell in the subject.

The method of the present invention may further comprise that the subject has or is suspected of having a sphingolipid-storage disorder (sphingolipidosis).

The method of the present invention may further comprise that the agent comprises the amino acid sequence set forth herein as SEQ ID NO: 1, or its encoding nucleic acid sequence. The method of the present invention may further comprise that the amino acid sequence of the functional variant of the Gdf1 protein has at least 95%, 96%, 97%, 98%, 99% identity to the sequence set forth herein as SEQ ID NO: 1. The method of the present invention may further comprise that the amino acid sequence of the functional variant of the Gdf1 protein has 1, 2, 3, 4, 5, 6, or more sequence modifications. The method of the present invention may further comprise that the sequence modifications are conservative amino acid substitutions.

The method of the present invention may further comprise that the agent comprises the amino acid sequence set forth herein as SEQ ID NO: 2, or its encoding nucleic acid sequence. The method of the present invention may further comprise that the amino acid sequence of the functional variant of the Gdf1 protein has at least 95%, 96%, 97%, 98%, 99% identity to the sequence set forth herein as SEQ ID NO: 2. The method of the present invention may further comprise that the amino acid sequence of the functional variant of the Gdf1 protein has 1, 2, 3, 4, 5, 6, or more sequence modifications. The method of the present invention may further comprise that the sequence modifications are conservative amino acid substitutions.

The composition of the method of the present invention may further comprise that one or more of a targeting agent, a delivery agent, a vector sequence, and a detectable label. Further, the method of the present invention may further comprise that the Gdf1 protein, Gdf1 functional variant, Gdf1 fragment, and Gdf1 fragment functional variant are part of a fusion protein.

In a third aspect, the present invention contemplates a method for determining a Gdf1 level in a biological sample, comprising: obtaining a biological sample from the subject and detecting one or more of a Gdf1 genomic transcript and a Gdf1 protein level in the biological sample. The method of the present invention may further comprise that the biological sample comprises one or more of a cell, a fluid, a bodily fluid, serum, blood, lymph, saliva, cerebral spinal fluid, and a tissue. The method of the present invention may further comprise that the subject has or is suspected of having one or more of: a malignancy, a neoplasia, a cancer, leukemia, or a precursor condition thereof. The method of the present invention may further comprise selecting a therapy for the subject, based at least in part on the detected gdf1 genomic transcript or Gdf1 protein in the biological sample. The method of the present invention may further comprise that the therapy comprises a ceramide-based therapy capable of increasing an endogenous ceramide mass levels. The method of the present invention may further comprise that the therapy comprises administering to the subject an exogenous ceramide compound or formulation that increases ceramide activity or mass levels in the subject. The method of the present invention may further comprise that the subject has or is suspected of having at least one abnormality in one or more of an epigenetic pathway and a splicesosome pathway.

In a fourth aspect, the present invention contemplates a kit suitable for detecting Gdf1 in a cell or other sample.

BRIEF DESCRIPTION OF THE DRAWINGS

FIG. 2A shows a histogram of unique patients with driver mutations against the mutations. FIG. 2B is a table showing the six mutations and their respective frequency and hazard ratios.

BRIEF DESCRIPTION OF THE SEQUENCES

Figure 1:
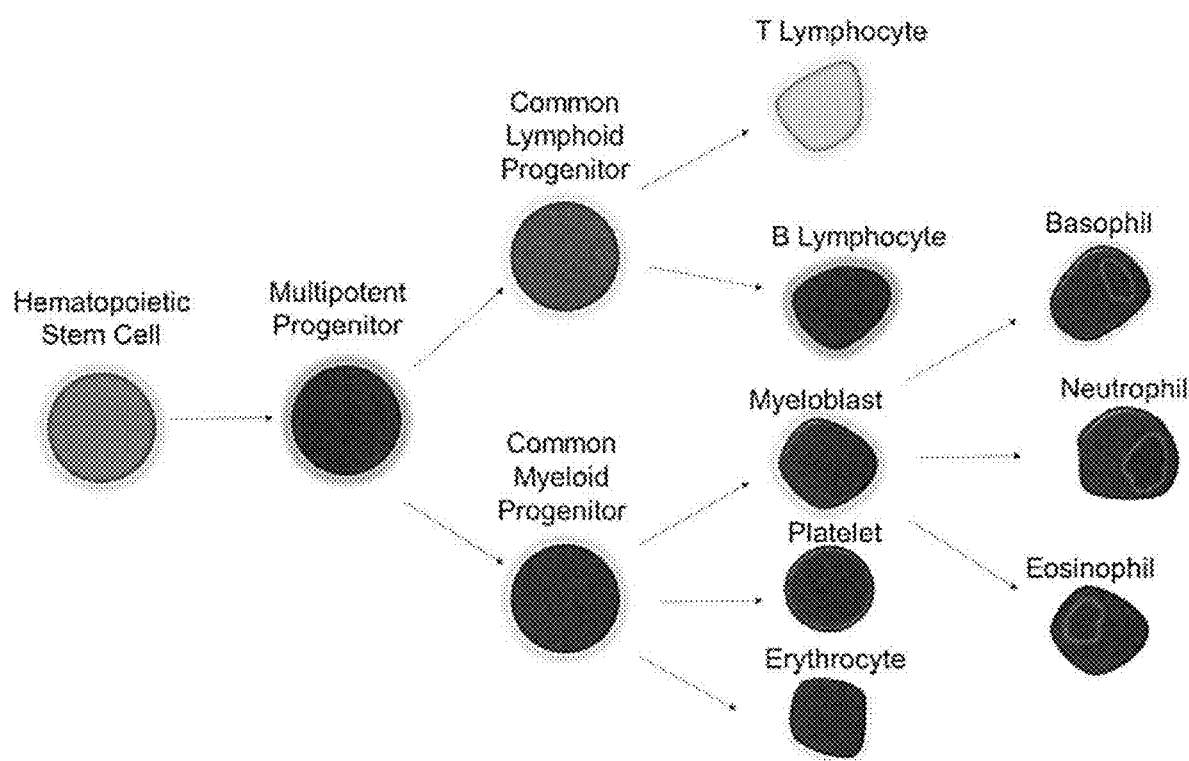
FIG. 1 shows hematopoietic cell differentiation.

SEQ ID NO: 1 is a 372 amino acid sequence of human Gdf1 protein having GenBank Accession No. NP_001483372.
MPPPQQGPCGHHLLLLLALLLPSLPLTRAPVPPGPAAALLQALGLRDEPQ
GAPRLRPVPPVMWRLFRRRDPQETRSGSRRTSPGVTLQPCHVEELGVAGN
IVRHIPDRGAPTRASEPASAAGHCPEWTVVFDLSAVEPAERPSRARLELR
FAAAAAAAPEGGWELSVAQAGQGAGADPGPVLLRQLVPALGPPVRAELLG
AAWARNASWPRSLRLALALRPRAPAACARLAEASLLLVTLDPRLCHPLAR
PRRDAEPVLGGGPGGACRARRLYVSFREVGWHRWVIAPRGFLANYCQGQC
ALPVALSGSGGPPALNHAVLRALMHAAAPGAADLPCCVPARLSPISVLFF
DNSDNVVLRQYEDMVVDECGCR.

SEQ ID NO: 2 is a fragment of SEQ ID NO: 1.
DAEPVLGGGPGGACRARRLYVSFREVGWHRWVIAPRGFLANYCQGQCALP
VALSGSGGPPALNHAVLRALMHAAAPGAADLPCCVPARLSPISVLFFDNS
DNVVLRQYEDMVVDECGCR.

SEQ ID NO: 3 is a human gdf1 probe.
5'/56-FAM/TCGTCTTC/ZEN/GACCTGTCGGCTGTGG/31ABkFQ/-3'

SEQ ID NO: 4 is a human gdf1 primer.
5'-CATTGCCCTGAGTGGACAG-3'

SEQ ID NO: 5 is a human gdf1 primer.
5'-GAAACGCAGCTCCAGGC-3'

SEQ ID NO: 6 is a human gdf1 probe.
5'-/56-FAM/CTTTGACAA/ZEN/CAGCGACAACGTGGTGC/31ABkFQ/-3'

SEQ ID NO: 7 is a humans gdf1 primer.
5'-CCCATCTCCGTGCTCTT-3'

SEQ ID NO: 8 is a human gdf1 primer.
5'-CACTCGTCCACCACCAT-3'

SEQ ID NO: 9 is a murine cers1 probe.
5'-/56-FAM/AACATTCTG/ZEN/CTGTTGCTCCTGATGGTCATG/31ABkFQ/-3'

SEQ ID NO: 10 is a murine cers1 primer.
5'-GCCTGACATTCCGTACTACTTC-3

SEQ ID NO: 11 is a murine cers1 primer.
5'-TCCAGTTCACGCATCTGAC-3'

DETAILED DESCRIPTION OF THE INVENTION

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Further, it is understood that the claim transitional phrases "consisting of," "consisting essentially of" and "comprising" have the meanings as give in MPEP 2111.03. In particular, the phrase "comprising essentially of" limits the scope of a claim to the specified materials or steps "and those that do not materially affect the basic and novel characteristic(s)" of the claimed invention and that any additional elements given in a dependent claim are not essential to the invention the inclusion of which do not materially affect the basic and novel characteristics of the claimed invention.

Further, the phrase "essentially equivalent" refers to one agent or item being equivalent in essential features but may have variation in non-essential features. Therefore, the phrase "essentially equivalent control cells" refers to cells of the same type used as an experimental control that are identical or nearly identical to the cells of the test condition with regard to the feature being tested. Usually, this means that the only known difference is the lack of the essentially equivalent control cells being subject to the experimental condition.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order that is logically possible.

Where numerical ranges are mentioned herein, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Where phrases such as "less than X", "greater than X", or "at least X" is used (where X is a number or percentage), it should be understood that any reasonable value can be selected as the lower or upper limit of the range. It is also understood that where a list of numerical values is stated herein (whether or not prefaced by "at least"), the invention includes embodiments that relate to any intervening value or range defined by any two values in the list, and that the lowest value may be taken as a minimum and the greatest value may be taken as a maximum.

Sphingolipids and Ceramide

Figure 3:
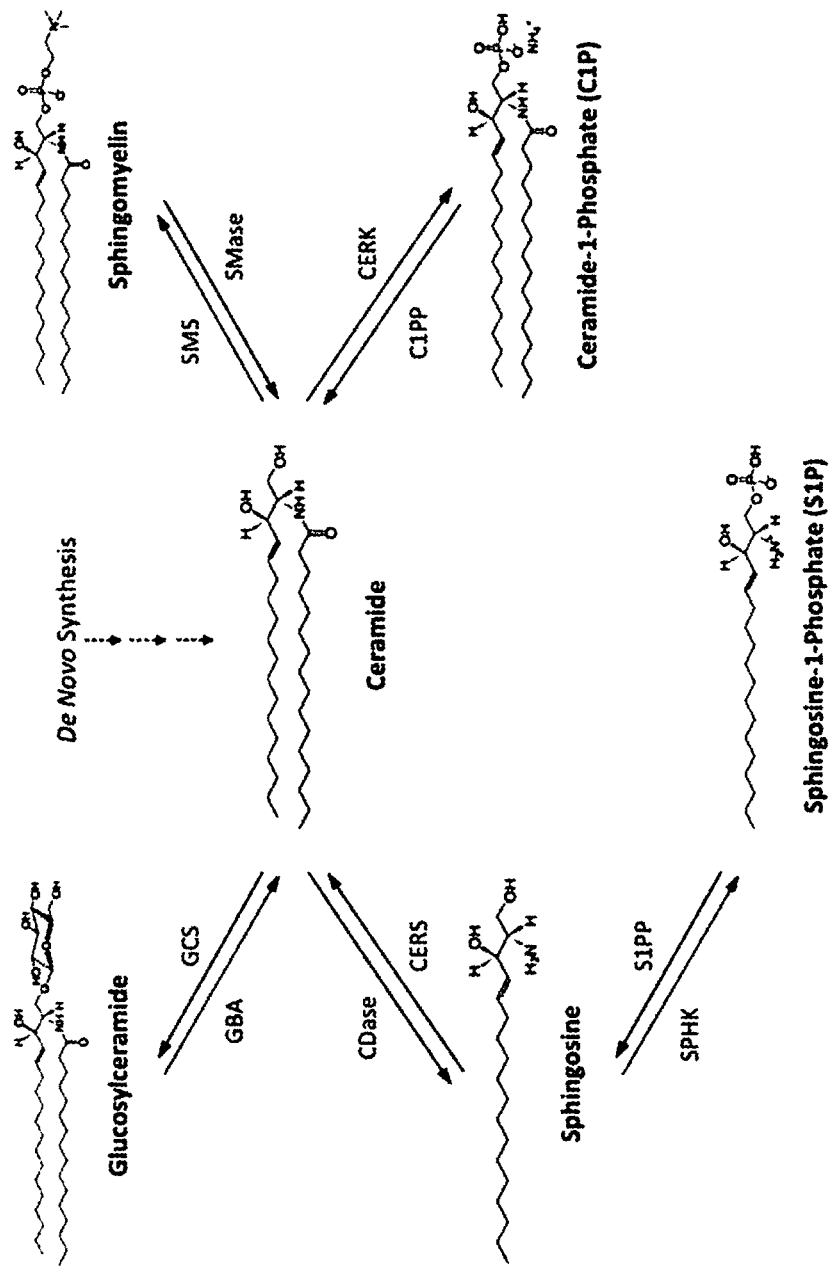
FIG. 3 shows ceramide metabolic pathways.

Sphingolipids are an extensive classification of lipids that play profound roles in membrane structure as well as regulation of cellular function and fate. See FIG. 1. Ceramide serves as the hypothetical center of sphingolipid metabolism, where it can serve as a precursor to a diversity of metabolites. Ceramide is a pro-apoptotic sphingolipid which exists in rheostat with its counterpart, pro-survival sphingosine-1-phosphate [Morad, S. & Cabot, M., Nature Reviews Cancer, 13:51-65 (2013)]. Several enzymes, such as glucosylceramide synthase (ugcg) and ceramidase (acid, Asah1), work to deplete the ceramide pool by converting ceramide to glucosylceramide and sphingosine, respectively. See, FIG. 3.

Intriguingly, ceramide regulates cellular stress responses and apoptosis, whereas many of its metabolites regulate opposing processes such as mitogenesis, proliferation and survival. Overall, there is great interest in sphingolipid metabolism given its broad relevance to various pathological conditions including cancer and a variety of metabolic and inflammatory conditions.

Interestingly, chemotherapy and radiation therapy has been shown to promote ceramide generation (Barth et al. Anticancer Agents Med Chem. 2011; 11:911-9). Similarly, ceramide deliver (Lip-C6, nanoliposomal ceramide) is a compound designed to promote apoptosis of malignant cells. In these situations, the upregulation of ceramide metabolism (i.e., the increased conversion of ceramide to its metabolites) neutralizes ceramide accumulation and becomes a pathway of therapy resistance since it is counterproductive to the goal of providing increased amounts of ceramide in a cell. Upregulation of ceramide metabolism may be governed by epigenetic mechanisms, rationalizing the utility of genetic or epigenetic-regulating therapies to restore ceramide sensitivity. The present invention is directed towards the use of Gdf1 to regulate ceramide metabolism via regulating (e.g., modulating or decreasing) ceramide neutralization in cells. In other words, the present invention is directed towards the use of Gdf1 to inhibit the neutralization of ceramide via ceramide metabolism making Gdf1 an agent suitable for increasing apoptosis in target cells. Furthermore, the present inventors have found that Gdf1 is effective in ending quiescence of and causing the differentiation of hemopoietic cancer stem cells thereby making them more susceptible to undergoing apoptosis due to Gdf1 ceramide neutralization and other anti-cancer therapies. Further still, since Gdf1 is a naturally occurring substance, toxicity effects common to synthetic agents may be reduced or eliminated.

GDF1

Figure 4:
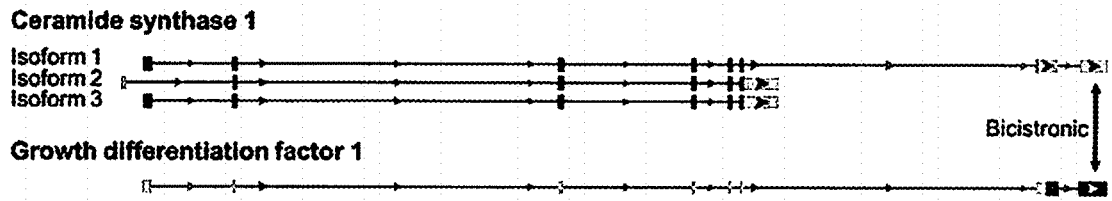
FIG. 4 shows the bicistronic transcript for ceramide synthase 1 and Gdf1.

Gdf1 is a BMP family member and TGF-beta signaling pathway intermediate. These proteins are known to play roles in stem cell and developmental biology. The gene encoding Gdf1 is a bicistronic transcript (see, FIG. 4; GenBank Accession No. 4332888.30 for the human bicistronic transcript), where, through a variation in splicing, Gdf1 or three isoforms of Cers1 may be produced. The full-length isoform of cers1 (human and mouse) is co-expressed with gdf1. Isoform 2 (human) has a distinct C-terminus where the opposite is true for the mouse isoform. Isoform 3, has a distinct N- and C-terminus, as well as an alternative promoter. Cers1 and gdf1 are differentially expressed on the AML TCGA dataset, which is a possible reason for observations attributing unique roles to Cers1 (and C18 ceramide).

The 372 amino acid sequence of human Gdf1 protein having GenBank Accession No. NP_001483372 is set forth herein as SEQ ID NO: 1, and this protein is also referred to in the art as: embryonic growth/differentiation factor 1 precursor. In humans, Gdf1 is encoded by the nucleotide sequence GenBank Accession No. 4332888.30, which is the sequence for the entire bicistronic gene. The amino acid sequence of an active fragment of Gdf1 that is used in certain aspects of the invention, is set forth herein as SEQ ID NO: 2. Additional human and non-human Gdf1 amino acid and nucleotide sequences are known in the art, are easily accessible via data bases such as GenBank (www.ncbi.nlm.nih.gov), and are incorporated herein by reference. In one aspect, the present invention is directed towards the modulation of ceramide neutralization in one or more cells by contacting the cell with one or more of an exogenous Gdf1 polypeptide or a vector encoding a Gdf1 polypeptide. The terms "protein" and "polypeptide" are used interchangeably herein. Gdf1 polypeptides of the present invention may be produced recombinantly.

Recombinant technology for producing polypeptides, including Gdf1 polypeptides are known and routinely used in the art. For example SEQ ID NO: 2 is commercially available (R&D Systems, Minneapolis, Minn.). Further, one of ordinary skill in the art would know how to clone the gdf1 gene into an expression vector for recombinant protein production and/or transfection. See, e.g., Sambrook, et al., Molecular Cloning, Fritsch and Maniatis, eds., Cold Spring Harbor Lab. Press, Cold Spring Harbor, N.Y. (1989) and subsequent revisions and below.

A composition that can be used in certain embodiments of methods of the invention to modulate ceramide neutralization in a cell and/or subject may comprise a Gdf1 polypeptide or a nucleic acid molecule that encodes a Gdf1 polypeptide or functional fragments thereof. A method of the invention may include administering an exogenous Gdf1 polypeptide or exogenous Gdf1 polypeptide-encoding nucleic acid to a subject. In some embodiments, the administered exogenous Gdf1 polypeptide may be a full-length Gdf1 polypeptide or may be a functional fragment of a full-length Gdf1 polypeptide that has Gdf1 function. In certain embodiments, the administered exogenous Gdf1 polypeptide-encoding nucleic acid may produce a Gdf1 polypeptide (full-length or fragment, or modified Gdf1 polypeptide) that has Gdf1 function. In another aspect of the invention, variants (i.e., deletions, additions or substitutions) of the peptide or nucleic acid encoding the peptide are contemplated.

GDF1 Variants

The term "variant" as applied to a particular polypeptide or active fragment thereof, refers to a polypeptide that differs from the subject polypeptide (sometimes referred to as the "original or native polypeptide or active fragment thereof") by one or more amino acid alterations, e.g., addition(s), deletion(s), and/or substitution(s). That is, the sequence is modified in some way. Sometimes an original polypeptide is a naturally occurring polypeptide (e.g., from human or non-human animal) or a polypeptide identical thereto. Variants may be naturally occurring or created using, e.g., recombinant DNA techniques or chemical synthesis. An addition can be an insertion within the polypeptide or an addition at the N- or C-terminus. In some embodiments, the number of amino acids substituted, deleted, or added can be for example, about 1 to 30, e.g., about 1 to 20, e.g., about 1 to 10, e.g., about 1 to 5, e.g., 1, 2, 3, 4, or 5. In some embodiments, a variant comprises a polypeptide whose sequence is homologous to the sequence of the original polypeptide over at least 50 amino acids, at least 100 amino acids, at least 150 amino acids, or more, up to the full length of the original polypeptide (but is not identical in sequence to the original polypeptide). For example, the sequence of the variant polypeptide is at least 75%, 80%, 85%, 90%, 95%, 96%, 97%, 98%, 99%, or more identical to the sequence of the original polypeptide over at least 50 amino acids, at least 100 amino acids, at least 150 amino acids, or more, up to the full length of the original polypeptide. In some embodiments, a variant comprises a polypeptide at least 75%, 80%, 85%, 90%, 91%, 92%, 93%, 94%, 95%, 96%, 97%, 98%, 99%, 99.5% or more identical to an original polypeptide over at least 75%, 80%, 85%, 90%, 91%, 92%, 93%, 94%, 95%, 96%, 97%, 98%, 99%, or 100% of the length of the original polypeptide. In some embodiments, a variant comprises at least one functional or structural domain, e.g., a domain identified as such in the Conserved Domain Database (CDD) of the National Center for Biotechnology Information (www.ncbi.nih.gov), e.g., an NCBI-curated domain.

In some embodiments of the invention one, more than one, or all biological functions or activities of a variant or fragment, which may be referred to herein as a "functional variant" or an "active fragment," respectively, is substantially similar to that of the corresponding biological function or activity of the original molecule. In some embodiments, a functional variant or active fragment retains at least 30%, 40%, 50%, 60%, 70%, 80%, 90%, 95%, 96%, 97%, 98%, 99%, or more up to 100% of the activity of the original polypeptide, e.g., about equal activity. In some embodiments, the activity of a variant or fragment is up to approximately 100%, approximately 125%, or approximately 150% of the activity of the original molecule. In other non-limiting embodiments of the invention, an activity of a variant or fragment is considered substantially similar to the activity of the original molecule if the amount or concentration of the variant needed to produce a particular effect is within 0.5 to 5-fold of the amount or concentration of the original molecule needed to produce that effect.

In some embodiments amino acid "substitutions" in a variant are the result of replacing one amino acid with another amino acid having similar structural and/or chemical properties, i.e., conservative amino acid replacements. "Conservative" amino acid substitutions may be made on the basis of similarity in any of a variety or properties such as side chain size, polarity, charge, solubility, hydrophobicity, hydrophilicity, and/or amphipathicity of the residues involved. For example, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid. Within a particular group, certain substitutions may be of particular interest, e.g., replacements of leucine by isoleucine (or vice versa), serine by threonine (or vice versa), or alanine by glycine (or vice versa). Of course, non-conservative substitutions are known in the art to be often compatible with retaining function as well. In some embodiments, a substitution or deletion does not alter or delete an amino acid important for activity. Insertions or deletions may range in size from about 1 to 20 amino acids, e.g., 1 to 10 amino acids. In some instances, larger domains may be removed without substantially affecting desired function. In certain embodiments of the invention the sequence of a variant can be obtained by making no more than a total of 5, 10, 15, or 20 amino acid additions, deletions, or substitutions to the sequence of a naturally occurring enzyme. In some embodiments no more than 1%, 5%, 10%, or 20% of the amino acids in a polypeptide are insertions, deletions, or substitutions relative to the original polypeptide. Guidance in determining which amino acid residues may be replaced, added, or deleted without eliminating or substantially reducing activities of interest, may be obtained by comparing the sequence of the particular polypeptide with that of homologous polypeptides (e.g., from other organisms) and minimizing the number of amino acid sequence changes made in regions of high homology (conserved regions) or by replacing amino acids with those found in homologous sequences since amino acid residues that are conserved among various species are more likely to be important for activity than amino acids that are not conserved.

If a particular polypeptide has more than one function, then "affecting desired function(s)" means changes that do or do not affect only the desired function(s). Other functions of the polypeptide may be changed without being considered beyond the scope of the present invention. For example, a variant may still retain a desired catalytic activity but not have native binding activity.

In some embodiments, a variant of a polypeptide comprises a heterologous polypeptide portion. The heterologous portion often has a sequence that is not present in or homologous to the original polypeptide. A heterologous portion may be, e.g., between 5 and about 5,000 amino acids long, or longer. Often it is between 5 and about 1,000 amino acids long. In some embodiments, a heterologous portion comprises a sequence that is found in a different polypeptide, e.g., a functional domain. In some embodiments, a heterologous portion comprises a sequence useful for purifying, expressing, solubilizing, and/or detecting the polypeptide. In some embodiments, a heterologous portion comprises a polypeptide "tag", e.g., an affinity tag or epitope tag. For example, the tag can be an affinity tag (e.g., HA, TAP, Myc, 6×His, Flag, GST), fluorescent or luminescent protein (e.g., EGFP, ECFP, EYFP, Cerulean, DsRed, mCherry), solubility-enhancing tag (e.g., a SUMO tag, NUS A tag, SNUT tag, or a monomeric mutant of the Ocr protein of bacteriophage T7). See, e.g., Esposito D and Chatterjee D K. Curr Opin Biotechnol.; 17(4):353-8 (2006). In some embodiments, a tag can serve multiple functions. A tag is often relatively small, e.g., ranging from a few amino acids up to about 100 amino acids long. In some embodiments a tag is more than 100 amino acids long, e.g., up to about 500 amino acids long, or more. In some embodiments, a polypeptide has a tag located at the N- or C-terminus, e.g., as an N- or C-terminal fusion. The polypeptide could comprise multiple tags. In some embodiments, a tag is cleavable, so that it can be removed from the polypeptide, e.g., by a protease. In some embodiments, this is achieved by including a sequence encoding a protease cleavage site between the sequence encoding the portion homologous to the original polypeptide and the tag. Cleavage sites and suitable proteases are known in the art. Sequences encoding a tag can be located 5' or 3' with respect to a polynucleotide encoding the polypeptide (or both). In some embodiments, a tag or other heterologous sequence is separated from the rest of the polypeptide by a polypeptide linker. For example, a linker can be a short polypeptide (e.g., 15-25 amino acids). Often a linker is composed of small amino acid residues such as serine, glycine, and/or alanine. A heterologous domain could comprise a transmembrane domain, a secretion signal domain, a targeting domain, etc. In some embodiments, mass spec tags comprising the naturally accruing N- and C-terminal amino acid residues use are specifically excluded from the present invention.

It will be understood that a composition of the invention may include a Gdf1 molecule and may also include additional components such as detectable labels, delivery agents, transfer moieties, vectors, etc. Additional components suitable for inclusion in a composition of the invention will be recognized by those skilled in the art and can be incorporated into compositions and methods of the invention using routine procedures.

Variants of the nucleic acid encoding a polypeptide of the present invention include any sequences that encode the polypeptide variants and fragments of the present invention. Further, nucleic acid substitutions that are redundant with respect to the genetic code are also considered an aspect by the present invention.

The term "vector" is used herein to refer to a nucleic acid or a virus or portion thereof (e.g., a viral capsid or genome) capable of mediating entry of, e.g., transferring, transporting, etc., a nucleic acid molecule into a cell. Where the vector is a nucleic acid, the nucleic acid molecule to be transferred is generally linked to, e.g., inserted into, the vector nucleic acid molecule. A nucleic acid vector may include sequences that direct autonomous replication (e.g., an origin of replication), or may include sequences sufficient to allow integration of part or all of the nucleic acid into host cell DNA. Useful nucleic acid vectors include, for example, DNA or RNA plasmids, cosmids, and naturally occurring or modified viral genomes or portions thereof or nucleic acids (DNA or RNA) that can be packaged into viral) capsids. Plasmid vectors typically include an origin of replication and one or more selectable markers. Plasmids may include part or all of a viral genome (e.g., a viral promoter, enhancer, processing or packaging signals, etc.). Viruses or portions thereof that can be used to introduce nucleic acid molecules into cells are referred to as viral vectors. Useful viral vectors include adenoviruses, adeno-associated viruses, retroviruses, lentiviruses, vaccinia virus and other poxviruses, herpesviruses (e.g., herpes simplex virus), and others. Viral vectors may or may not contain sufficient viral genetic information for production of infectious virus when introduced into host cells, i.e., viral vectors may be replication-defective, and such replication-defective viral vectors may be preferable for therapeutic use. Where sufficient information is lacking it may, but need not be, supplied by a host cell or by another vector introduced into the cell. The nucleic acid to be transferred may be incorporated into a naturally occurring or modified viral genome or a portion thereof or may be present within the virus or viral capsid as a separate nucleic acid molecule. It will be appreciated that certain plasmid vectors that include part or all of a viral genome, typically including viral genetic information sufficient to direct transcription of a nucleic acid that can be packaged into a viral capsid and/or sufficient to give rise to a nucleic acid that can be integrated into the host cell genome and/or to give rise to infectious virus, are also sometimes referred to in the art as viral vectors. Vectors may contain one or more nucleic acids encoding a marker suitable for use in the identifying and/or selecting cells that have or have not been transformed or transfected with the vector. Markers include, for example, proteins that increase or decrease either resistance or sensitivity to antibiotics (e.g., an antibiotic-resistance gene encoding a protein that confers resistance to an antibiotic such as puromycin, hygromycin or blasticidin) or other compounds, enzymes whose activities are detectable by assays known in the art (e.g., beta.-galactosidase or alkaline phosphatase), and proteins or RNAs that detectably affect the phenotype of transformed or transfected cells (e.g., fluorescent proteins). Expression vectors are vectors that include regulatory sequence(s), e.g., expression control sequences such as a promoter, sufficient to direct transcription of an operably linked nucleic acid. Regulatory sequences may also include enhancer sequences or upstream activator sequences. Vectors may optionally include 5' leader or signal sequences. Vectors may optionally include cleavage and/or polyadenylations signals and/or a 3' untranslated regions. Vectors often include one or more appropriately positioned sites for restriction enzymes, to facilitate introduction into the vector of the nucleic acid to be expressed. An expression vector comprises sufficient cis-acting elements for expression; other elements required or helpful for expression can be supplied by the host cell or in vitro expression system. Vectors useful in some methods of the invention can genetically insert Gdf1 polypeptides into dividing and non-dividing cells and can insert Gdf1 polypeptides to cells that are in vivo, in vitro, or ex vivo cells.

Various techniques may be employed for introducing nucleic acid molecules into cells. Such techniques include chemical-facilitated transfection using compounds such as calcium phosphate, cationic lipids, cationic polymers, liposome-mediated transfection, non-chemical methods such as electroporation, particle bombardment, or microinjection, and infection with a virus that contains the nucleic acid molecule of interest (sometimes termed "transduction"). Markers can be used for the identification and/or selection of cells that have taken up the vector and, typically, express the nucleic acid. Cells can be cultured in appropriate media to select such cells and, optionally, establish a stable cell line.

Vectors useful in methods of the invention may include additional sequences including, but not limited to one or more signal sequences and/or promoter sequences, or a combination thereof. Expression vectors and methods of their use are well known in the art. In certain embodiments of the invention, a vector may be a lentivirus comprising a nucleic acid or gene that encodes a Gdf1 polypeptide of the invention or a variant thereof. A lentivirus is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of an Gdf1 polypeptide in a wide variety of cell types—thus a promoter for a gene that is widely expressed in a variety of cell types, for example a "housekeeping gene" can be used to express a Gdf1 polypeptide in a variety of cell types. Non-limiting examples of general promoters are provided elsewhere herein and suitable alternative promoters are well known in the art. In certain embodiments of the invention, a promoter may be an inducible promoter, examples of which include, but are not limited to tetracycline-on or tetracycline-off, etc.

Certain aspects of the invention include methods of administering a Gdf1 molecule such as a Gdf1 polypeptide or functional fragment thereof, or a Gdf1-encoding nucleic acid, etc., to treat an angiogenic or immune system disease or condition characterized by abnormally low Gdf1 polypeptide activity.

GDF1 Probes/Primers

Certain aspects of the present invention include probes and primers specific for human gdf1. As discussed above, the gdf1 gene is a bicistronic gene that encode multiple isoforms. SEQ ID NOS: 3 and 6 encode human gdf1 probes and SEQ ID NOS: 4, 5, 7 and 8 encode human gdf1 primers. In the context of the present invention, the probes and primers are designed to only detect the isoform encoding gdf1. This is in sharp contrast to prior art marketed probes and primers, which detect all isoforms of the gene sequence.

Likewise, SEQ ID NOS: 9 encodes a murine cers1 probe and SEQ ID NOS: 10 and 11 encode murine cers1 primers. Like its human counterpart, the murine gene also codes various isoforms, as discussed above.

One of ordinary skill in the art understands the use of probes and primers in detecting and amplifying the nucleic acid encoding the target genes. In the context of the present invention, the probes and primers are designed to only detect the isoform encoding human gdf7 (or murine cers1). This is in sharp contrast to prior art marketed probes and primers, which detect all isoforms of the gene sequences.

One of ordinary skill in the art understands the use of probes and primers for the detection of target gene sequences and amplification of the gene sequence, the use of which is disclosed in standard technical references such as Sambrook, et al., Molecular Cloning, Fritsch and Maniatis, eds., Cold Spring Harbor Lab. Press, Cold Spring Harbor, N.Y. (1989) and subsequent revisions.

Diseases Associated with Ceramide Neutralization

Ceramide neutralization has been associated with diseases that manifest themselves through increase proliferation and/or decreased programmed cell death (apoptosis). Cancers, especially cancers such a leukemia, are likely targets of therapy directed towards ceramide neutralization. Hematopoietic stem cells, found in the bone marrow and lymph organs, undergo an initial differentiation step to form lymphoid and myeloid progenitors. See, FIG. 1. These progenitor cells undergo further differentiation and proliferation to produce the shown components of blood. Mutations in progenitor cells can result in hematopoietic disorders and malignancies, such as Myelodysplastic syndrome and Acute Myeloid Leukemia (AML).

The present invention contemplates that other cancers may be susceptible to ceramide neutralization such as, but not limited to, Bladder Cancer, Breast Cancer, Colon and rectal cancer, endometrial cancer, kidney cancer, liver cancer, lung cancer, melanoma, non-hodgkin lymphoma, pancreatic cancer, prostate cancer and thyroid cancer.

Figure 2:
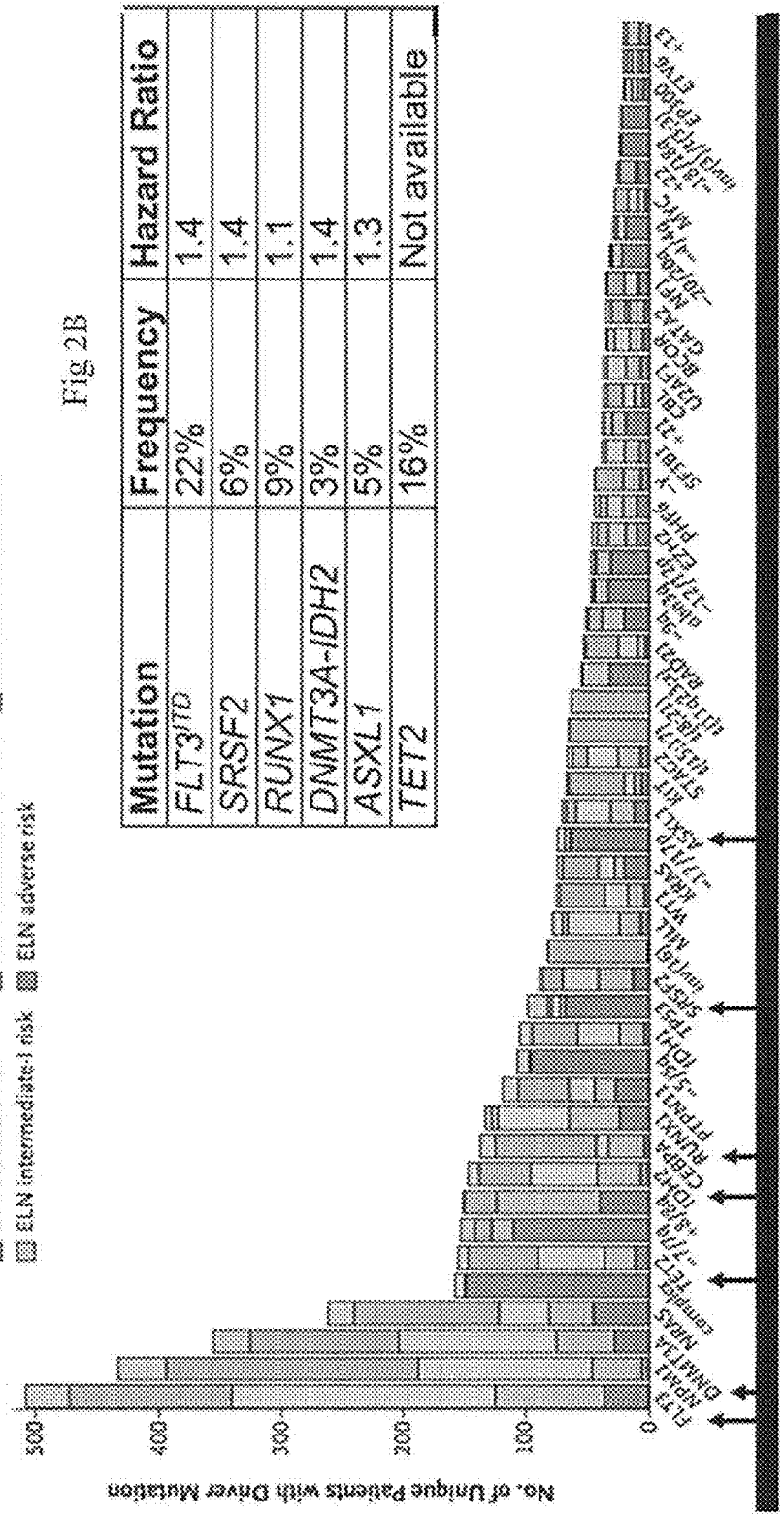
FIG. 2A-B shows mutations associated with acute myeloid leukemia.

Acute myeloid leukemia is a highly heterogeneous disease, with more than 5,000 driver mutations across 76 genes [Papaemmanull, E., et al., NEJM, 374, 2209-2221 (2016)]. See, FIG. 2A. Mutations in genes encoding epigenetic regulators, such as Dnmt3A, Asxl1, and Tet2, are relatively common in patients and result in negative survival outcomes. See FIG. 2B. Similar patterns are observed for patients carrying mutations in genes encoding splicing factors, such as Srsf2 and Rura1.

In AML, there is a prevalence of mutations to epigenetic regulators that are commonly associated with poor clinical outcomes. Therefore, there is great interest in understanding links between epigenetic dysfunction and the underlying pathobiology of AML. In a similar manner, recent studies have sought to define the underlying mechanisms responsible for dysfunctional sphingolipid metabolism that has been observed in AML in order to improve the anti-AML efficacy of sphingolipid-based therapeutics. The present invention is directed towards a role for epigenetic regulation of sphingolipid metabolism via therapeutic intervention with Gdf1 in AML in general and the regulation of ceramide neutralization by Gdf1 in particular to effect a positive outcome in decreasing AML cell viability.

Myelodysplastic syndromes (MDS) are a family of rare disorders in which the bone marrow fails to make enough healthy red blood cells, white blood cells or platelets. This is caused when the bone marrow produces underdeveloped or immature cells that are often identifiable because of an abnormal shape, size or other appearance. Most experts agree that MDS is a form of blood and bone marrow cancer. While there are many subtypes of MDS, all carry a high risk of becoming acute myelogenous leukemia. Sphingolipidoses (singular "sphingolipidosis") are a class of lipid storage disorders relating to sphingolipid metabolism. The main members of this group are Niemann-Pick disease, Fabry disease, Krabbe disease, Gaucher disease, Tay-Sachs disease and metachromatic leukodystrophy. They are generally inherited in an autosomal recessive fashion, but notably Fabry disease is X-linked recessive. Taken together, sphingolipidoses have an incidence of approximately 1 in 10,000, but substantially more in certain populations such as Ashkenazi Jews. Enzyme replacement therapy is available to treat mainly Fabry disease and Gaucher disease, and people with these types of sphingolipidoses may live well into adulthood. The other types are generally fatal by age 1 to 5 years for infantile forms, but progression may be mild for juvenile- or adult-onset forms.

Administration Methods

A variety of administration routes for a ceramide neutralization-modulating compound are available. The particular delivery mode selected will depend, of course, upon the particular condition being treated and the dosage required for therapeutic efficacy. Methods of this invention, generally speaking, may be practiced using any mode of administration that is medically acceptable, meaning any mode that produces effective levels of protection without causing clinically unacceptable adverse effects. In some embodiments of the invention, a compound of the invention may be administered via an oral, enteral, mucosal, percutaneous, and/or parenteral route. The term "parenteral" includes subcutaneous, intravenous, intramuscular, intraperitoneal, and intrasternal injection, or infusion techniques. Other routes include but are not limited to nasal (e.g., via a gastro-nasal tube), dermal, vaginal, rectal, and sublingual. Delivery routes of the invention may include intrathecal, intraventricular, or intracranial. In some embodiments of the invention, a compound of the invention may be placed within a slow release matrix and administered by placement of the matrix in the subject. In some aspects of the invention, a compound (such as a Gdf1 polypeptide-encoding nucleic acid, Gdf1 polypeptide or functional variant thereof, Gdf1 active fragment or functional variant thereof, or a small molecule Gdf1 or enhancer, etc.) may be delivered to a subject cell using nanoparticles coated with or without a delivery agent that targets a specific cell or tissue. In that regard, compounds and agents of the present invention may be encapsulated or incorporated into particles, e.g., microparticles or nanoparticles. Biodegradable, biocompatible polymers can be used, such as ethylene vinyl acetate, polyanhydrides, polyglycolic acid, PLGA, collagen, polyorthoesters, polyethers and polylactic acid. Methods for preparation of such formulations will be apparent to those skilled in the art. For example, and without limitation, a number of particle, lipid, and/or polymer-based delivery systems are known in the art for delivery of siRNA. The invention contemplates use of such compositions. Liposomes or other lipid-based particles such as nanoliposomes (e.g., nanoliposomal C6-ceramide: "Lip-C6") and nanocolloids can also be used as pharmaceutically acceptable carriers.

Compounds of the invention may be administered in formulations, which may be administered in pharmaceutically acceptable solutions, which may routinely contain pharmaceutically acceptable concentrations of salt, buffering agents, preservatives, compatible carriers, adjuvants, and optionally other therapeutic ingredients. According to methods of the invention, the compound may be administered in a pharmaceutical composition. In general, a pharmaceutical composition comprises the compound of the invention and a pharmaceutically-acceptable carrier. Pharmaceutically-acceptable carriers are well-known to those of ordinary skill in the art. As used herein, a pharmaceutically-acceptable carrier means a non-toxic material that does not interfere with the effectiveness of the biological activity of the active ingredients, e.g., the ability of the compound such as a Gdf1 polypeptide-encoding nucleic acid, Gdf1 polypeptide, or a small molecule Gdf1 enhancer, etc., to a disease or condition amenable to ceramide modulation or neutralization.

Pharmaceutically acceptable carriers include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Compounds of the invention may be administered directly to a tissue. In some embodiments, the tissue to which the compound is administered is cancerous. Direct tissue administration may be achieved by direct injection. Compounds may be administered once, or alternatively they may be administered in a plurality of administrations. If administered multiple times, the compounds may be administered via different routes. For example, the first (or the first few) administrations may be made directly into the affected tissue while later administrations may be systemic.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with or without an added preservative. The compositions may take such forms as suspensions, solutions or emulsions in oily or aqueous vehicles, and may contain formulatory agents such as suspending, stabilizing and/or dispersing agents.

Preparations for parenteral administration may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day may be used as needed to achieve appropriate systemic or local levels of compounds.

In yet other embodiments, a delivery vehicle is a biocompatible microparticle or implant that is suitable for implantation into the mammalian recipient. Exemplary bioerodible implants that are useful in accordance with this method are described in PCT Publication No. WO 95/24929 (incorporated by reference herein), which describes a biocompatible, biodegradable polymeric matrix for containing a biological macromolecule. Such delivery means are well known in the art and can be used to achieve sustained release of a compound of the invention in a subject, and may be selected not to degrade, but rather, to release by diffusion over an extended period of time.

Both non-biodegradable and biodegradable polymeric matrices can be used to deliver the compounds of the invention to the subject. In some embodiments, a matrix may be biodegradable. Matrix polymers may be natural or synthetic polymers. A polymer can be selected based on the period of time over which release is desired, generally in the order of a few hours to a year or longer. Typically, release over a period ranging from between a few hours and three to twelve months can be used. The polymer optionally is in the form of a hydrogel that can absorb up to about 90% of its weight in water and further, optionally is cross-linked with multivalent ions or other polymers.

In general, compounds of the invention may be delivered using the bioerodible implant by way of diffusion, or by degradation of the polymeric matrix. Exemplary synthetic polymers for such use are well known in the art. Biodegradable polymers and non-biodegradable polymers can be used for delivery of compounds of the invention using art-known methods. Bioadhesive polymers such as bioerodible hydrogels (see H. S. Sawhney, C. P. Pathak and J. A. Hubell in Macromolecules, 1993, 26, 581-587, the teachings of which are incorporated herein) may also be used to deliver compounds of the invention for treatment. Additional suitable delivery systems can include time-release, delayed release or sustained release delivery systems. Such systems can avoid repeated administrations of the compound, increasing convenience to the subject and the physician. Many types of release delivery systems are available and known to those of ordinary skill in the art. (See for example: U.S. Pat. Nos. 5,075,109; 4,452,775; 4,675,189; 5,736,152; 3,854,480; 5,133,974; and 5,407,686 (the teaching of each of which is incorporated herein by reference). In addition, pump-based hardware delivery systems can be used, some of which are adapted for implantation.

Use of a long-term sustained release implant may be particularly suitable for treatment of subjects with invasive or otherwise hard to treat conditions. Long-term release, as used herein, means that the implant is constructed and arranged to delivery therapeutic levels of the active ingredient for at least 30 days, 60 days, 90 days or longer. Long-term sustained release implants are well-known to those of ordinary skill in the art and include some of the release systems described above.

Therapeutic formulations of compounds of the invention may be prepared for storage by mixing the compound having the desired degree of purity with optional pharmaceutically acceptable carriers, excipients or stabilizers [Remington's Pharmaceutical Sciences 21st edition, (2006)], in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Additional Gdf1-Activity-Enhancing Compounds

Additional compounds that may be administered in treatment methods of the invention include small molecules or chemicals that enhance or augment Gdf1 polypeptide activity. Methods of identifying and testing such small molecules and chemicals may include use of art-known library screening and testing procedures in conjunction with the teaching provided herein.

It will be understood that in addition to compounds set forth herein, additional Gdf1-modulating compounds can be identified and used in methods of the invention. For example, candidate compounds can be can be tested for their ability to increase or augment Gdf1 polypeptide activity (level and/or function) and their ability to treat a cancerous conditions including AML as well as myelodysplastic syndromes and sphingolipidoses using compositions and methods presented herein. Anti-cancer drugs (i.e., chemotherapy medications) and agents that modulate ceramide neutralization are in combination with Gdf1 are aspects of the present invention. One such compound is decitabine (5-aza-2'-deoxycytidine). Other hypomethylating agents can also be used in embodiments of methods of the invention. Non-limiting examples of hypomethylating agents are: azacitidine (ArcC). Other hypomethylating agents as known in the art are useful in combination with the invention of the present invention.

Gdf1-Activity-Enhancing Compound Administration

Gdf1 peptide and Gdf1 polypeptide modulating compounds of the invention may be administered singly or in combination with one or more additional compounds. In some embodiments, a compound of the invention may act in a synergistic manner with one or more other therapeutic agents or treatments and increase the effectiveness of the one or more therapeutic agents or activities, thus a Gdf1 enhancer compound may act synergistically to increase the effectiveness of one or more agents or treatments that can be administered to treat conditions amenable to modulating and/or reducing ceramide neutralization.

Compositions, compounds, and methods of the invention may be enhanced by utilization in combination with other procedures for modulating and/or reducing ceramide neutralization. In some instances a treatment procedure may involve administration of another therapeutic agent or treatment such a medicament and/or a behavioral treatment, surgery, etc. Thus, in some embodiments of the invention, administration of a compound of the invention (e.g., administration of a Gdf1 polypeptide-encoding nucleic acid, Gdf1 polypeptide (or functional fragment thereof), or a small molecule Gdf1 enhancer, etc.) may be performed in conjunction with therapies for treating conditions amenable to modulating and/or reducing ceramide neutralization. Treatment methods of the invention that include administration of a Gdf1-modulating compound can be used at any stage of, for example, cancer, especially leukemia. Methods of the invention may also be used for subjects who have previously been treated with one or more other medicaments or therapy methods that were not successful, were minimally successful, and/or are no longer successful at slowing or stopping progression of the target disease or disorder in the subject.

Gdf1-modulating compounds of the invention (such as compounds comprising a functional Gdf1 molecule, a small molecule Gdf1 enhancer, etc.) described herein can be used alone or in conjugates with other molecules such as targeting agents, labeling agents, and/or cytotoxic agents in treatment methods of the invention.

Targeting agents useful according to the methods of the invention are those that direct a compound of the invention to a specific cell type, an example of which, though not intended to be limiting are cancer cells. Those of ordinary skill in the art will be aware of and able to select and use suitable targeting agents for use in methods of the invention.

Labeling agents may be used in methods of the invention to determine the location of Gdf1 polypeptides in cells and tissues and also, may be used to assess the cell, tissue, or organelle location of treatment compounds that have been administered. Non-limiting examples of labeling agents are: fluorescent molecules, luminescent molecules, colorimetric moieties, etc. Identifying suitable labeling agents and procedures for attaching and utilizing labeling agents such as enzymatic labels, dyes, radiolabels, etc. are well known in the art.

Effective Amounts for Treatments

Gdf1-modulating compounds of the invention, (e.g., a Gdf1 polypeptide-encoding nucleic acid, Gdf1 polypeptide, or a small molecule Gdf1 enhancer, etc.) are administered to the subject in an effective amount for treating the disease or condition amenable to ceramide modulation or neutralization. An "effective amount" for treating disease or condition amenable to ceramide modulation or neutralization is an amount necessary or sufficient to realize a desired biologic effect. For example, an effective amount of a compound of the invention could be that amount necessary to (i) slow or halt progression of the disease or condition; or (ii) reverse one or more symptoms of the disease or condition. According to some aspects of the invention, an effective amount is that amount of a compound of the invention alone or in combination with another medicament or treatment, which when combined or co-administered or administered alone, results in a therapeutic response in the disease or condition amenable to ceramide modulation or neutralization. The biological effect may be the amelioration and or absolute elimination of symptoms resulting from the disease or condition amenable to ceramide modulation or neutralization.

Typically an effective amount of a compound or drug to increase the function or level of a Gdf1 polypeptide will be determined in clinical trials, establishing an effective dose for a test population versus a control population in a blind study. In some embodiments, an effective amount will be that results in a desired response, e.g., an amount that diminishes one or more symptoms of a disease or condition amenable to ceramide modulation or neutralization. Thus, an effective amount to treat a disease or condition characterized by a ceramide neutralization may be the amount that when administered to the subject, cell or tissue to an amount that that is above the amount that would occur in the subject, cell, or tissue, respectively without the administration of the composition. In the case of treating a disease or condition amenable to ceramide modulation or neutralization, the desired response may be reducing or eliminating one or more symptoms of the disease or condition in the cell, tissue, and/or subject. The reduction or elimination may be temporary or may be permanent. The status of the disease or condition can be monitored using methods of ceramide neutralization or levels of molecules activated by DF1, such as UGCG and SGMS1.

An effective amount of a compound that modulates or regulates (e.g., reduces) ceramide neutralization (also referred to herein as a pharmaceutical compound) may also be determined by assessing physiological effects of administration on a cell or subject, such as a decrease of cancer or remission. Assays suitable to determine efficacy of a pharmaceutical compound of the invention will be known to those skilled in the art and can be employed for measuring the level of the response to a treatment and an amount of a pharmaceutical compound administered to a subject can be modified based, at least in part, on such measurements. The amount of a treatment may be varied for example by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated; the severity of the condition, the duration of the treatment, the nature of the concurrent therapy (if any), the specific route of administration, and additional factors within the knowledge and expertise of the health practitioner.

The effective amount of a compound of the invention may vary depending upon the specific compound used (polypeptide or nucleic acid), the mode of delivery of the compound, and whether it is used alone or in combination with other agents. The effective amount for any particular application can also vary depending on such factors as the disease or condition amenable to ceramide modulation or neutralization being treated, the size of the subject, or the severity of the disease or condition. A skilled artisan can empirically determine the effective amount of a particular compound of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

A pharmaceutical compound dosage may be adjusted by an individual health care provider or veterinarian, particularly in the event of any complication. A therapeutically effective amount typically varies from 0.01 mg/kg to about 1000 mg/kg, from about 0.1 mg/kg to about 200 mg/kg, or from about 0.2 mg/kg to about 20 mg/kg, in one or more dose administrations daily, for one or more days. The absolute amount will depend upon a variety of factors including a concurrent treatment, the number of doses and the individual subject parameters including age, physical condition, size and weight. These are factors well known to those of ordinary skill in the art and can be addressed with no more than routine experimentation. In some embodiments, a maximum dose can be used, that is, the highest safe dose according to sound medical judgment.

Multiple doses of compounds of the invention are also contemplated. In some instances, a compound of the invention, (e.g., a Gdf1 polypeptide-encoding nucleic acid, Gdf1 polypeptide, or a small molecule Gdf1 effect enhancer, etc.) can be administered at least daily, every other day, weekly, every other week, monthly, etc. Doses may be administered once per day or more than once per day, for example, 2, 3, 4, 5, or more times in one 24 hour period.

Pharmaceutical compounds of the invention may be administered alone, in combination with each other, and/or in combination with other drug therapies, or other treatment regimens that are administered to target subjects. Pharmaceutical compositions used in the foregoing methods preferably are sterile and contain an effective amount of a therapeutic compound that will modulate ceramide neutralization to a level sufficient to produce the desired response in a unit of weight or volume suitable for administration to a subject.

The doses of a composition to modulate ceramide neutralization that is administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

Assessing Treatments of a Disease or Condition Amenable to Ceramide Modulation or Neutralization In some aspects of the invention methods are provided that include comparing a level of ceramide or one or more components of the ceramide synthesis or degradation pathway in a sample obtained from a subject to a control value for determining the efficacy of a treatment of the invention. In addition, the effectiveness of a treatment of the invention can be assessed by measuring Gdf1 levels in samples obtained from a subject to monitor administration of agent(s) of the invention. Thus, methods of the invention, in some aspects, include assessing the onset, progression, or regression of an a disease or condition amenable to ceramide modulation or neutralization, by measuring ceramide neutralization levels or disease symptoms in samples obtained from or tested in the subject at two, three, four, five, or more different times, e.g., before, during and after a treatment regimen of the invention. Thus, for example, in a method that utilizes two or more samples obtained from a subject at different times, values obtained from a sample obtained at one time can be compared to values obtained at other times as a measure of the efficacy of a treatment of the invention.

The invention, in some aspects, includes methods and assays (e.g. binding assays, gel electrophoresis; mass spectrometry; NMR; etc.) to determine changes in ceramide neutralization in a subject or cell sample (e.g., cell culture) over time. This allows monitoring of ceramide neutralization in a subject who is to undergo a treatment of the invention.

Exemplification

The following exemplification is considered non-limiting. It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

Figure 5:
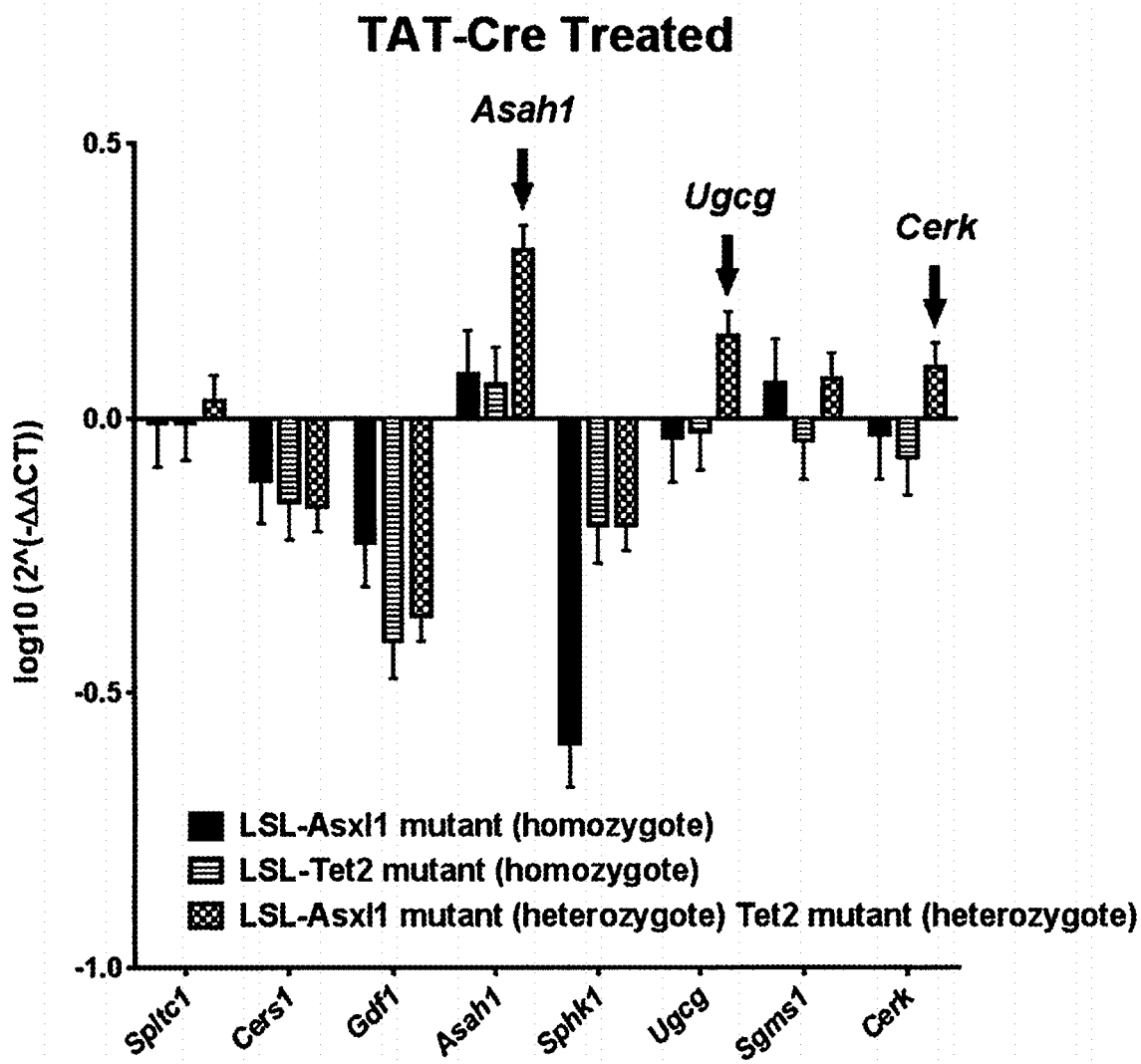
FIG. 5 shows that mutational cooperativity between Asxl1 and Tet2 lead to an upregulation of ceramide metabolism.

Mutational cooperativity between Asxl1 and Tet2 led to an upregulation of ceramide metabolism. Splenocytes were treated with TAT-Cre recombinase at a concentration of 44 µM for 7 days to induce mutant transgene expression. Results were generated via quantitative real time PCR (qRT-PCR) and normalized to the housekeeping genes for beta actin (Actb), RNA polymerase II (RpII), and TATA-box binding protein (Tbp). As shown in FIG. 5, while mutations in Asxl1 or Tet2 alone did not alter expression of ceramide metabolic enzymes, mutational cooperativity resulted in upregulation of both ugcg and Asah1. Mutant Asxl1, Tet2, and combined Asxl1-Tet2 all resulted in downregulation of cers1.

For all TAT-Cre experiments (here and below), the splenocytes were harvested from transgenic mice. The transgenic mouse strains that were no generated in-house were obtained from Jackson lab, Bar Harbor, Me.:

Asxl1 mutant mice: STOCK Asxl1tm1.1Iaai/J (www.jax.org/strain/025665).
Flt3-ITD mice: B6.129-Flt3tm1Dgg/J (www.jax.org/strain/011112).
Tet2 mutant mice: B6; 129S-Tet2tm1.1Iaai/J (www.jax.org/strain/017573).
Srsf2 mutant mice: B6J.B6NTac(SJL)-Srsf2tm1.1Oaw/J (www.jax.org/strain/028376).
Asxl1-Tet2 mutant mice: we generated these in-house by crossing Asxl1 mutant mice with Tet2 mutant mice.

Figure 6:
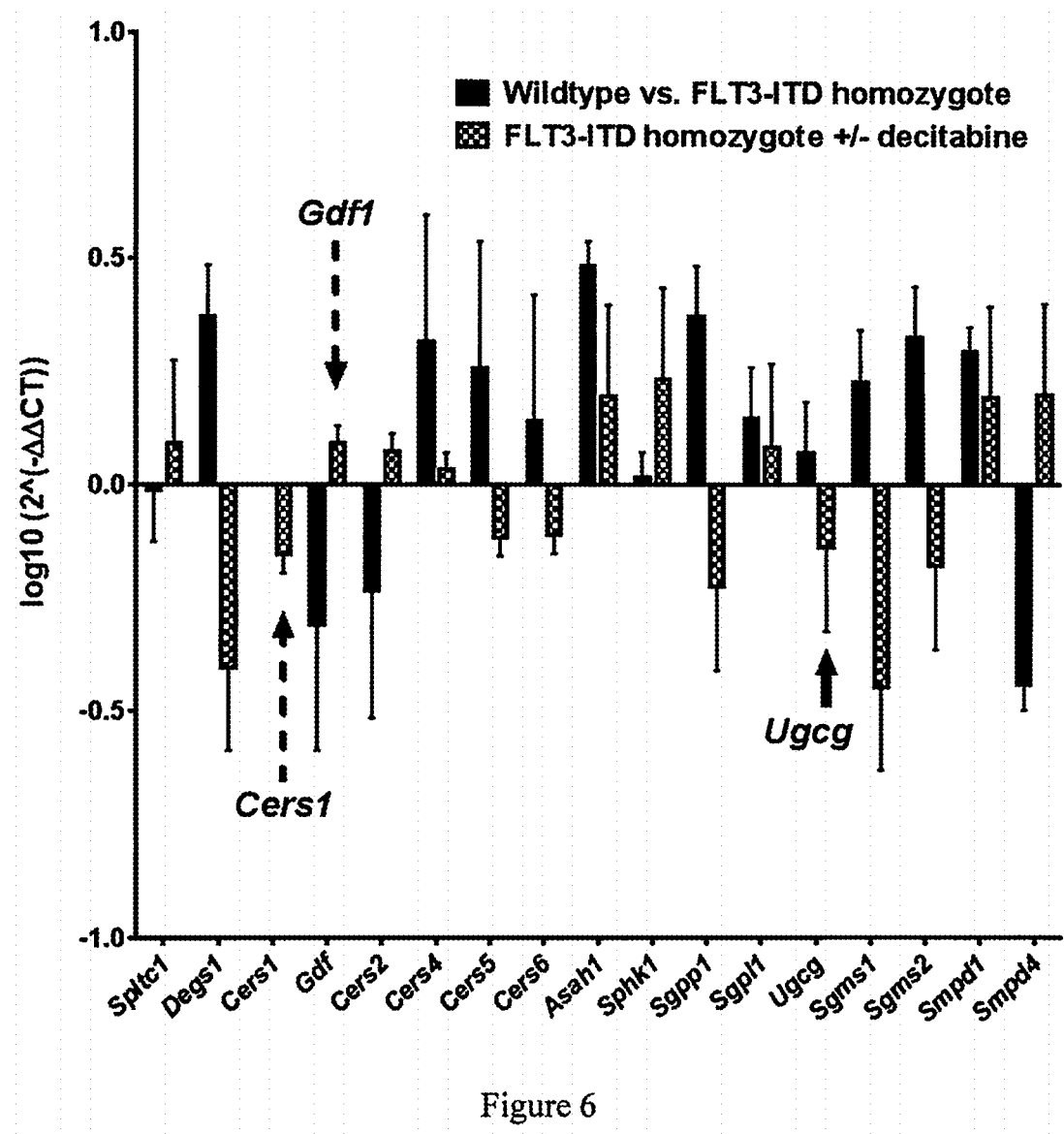
FIG. 6 shows that decitabine treatment downregulates ceramide neutralization in FLT3$^{ITD}$ transgenic mice while augmenting gdf1 expression.

Decitabine treatment downregulates ceramide neutralization in FLT3$^{ITD}$ transgenic mice while augmenting gdf1 expression. 8-12 week old mice harboring an internal tandem duplication in the Flt3 gene were treated with the hypomethylating agent, decitabine, at 0.2 mg/kg, 3 times weekly, for 6 weeks. Results were generated using qRT-PCR and normalized to housekeeping genes (Actb, RpII, Tbp). As shown in FIG. 6, mice homozygous for F/t3$^{ITD}$ displayed upregulation of ugcg and Asah1, as compared to wild-type counterparts. Treatment with decitabine reversed ugcg expression and led to downregulation of cers1 as compared to control mice. Interestingly, gdf1 expression was upregulated with treatment of decitabine. As expected, other related genes are also affected by decitabine treatment.

Figure 7:
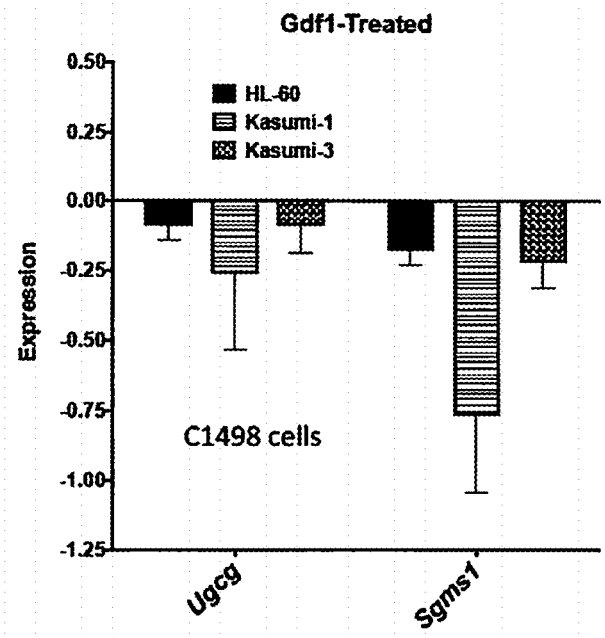
FIG. 7 shows that Gdf1 treatment of AML cell lines triggers downregulation of ceramide neutralization pathways.

Gdf1 treatment of AML cell lines triggers downregulation of ceramide neutralization pathways. AML cell lines (HL-60, Kasumi-1 and Kasumi-3), were treated with recombinant human gdf1 at a concentration of 50 ng/mL for 24 hours. Results were obtained via qRT-PCR and compared to housekeeping genes (Actb, RpII). As shown in FIG. 7, cers1 and ugcg were downregulated with the addition of Gdf1 as compared to untreated counterparts.

Figure 8:
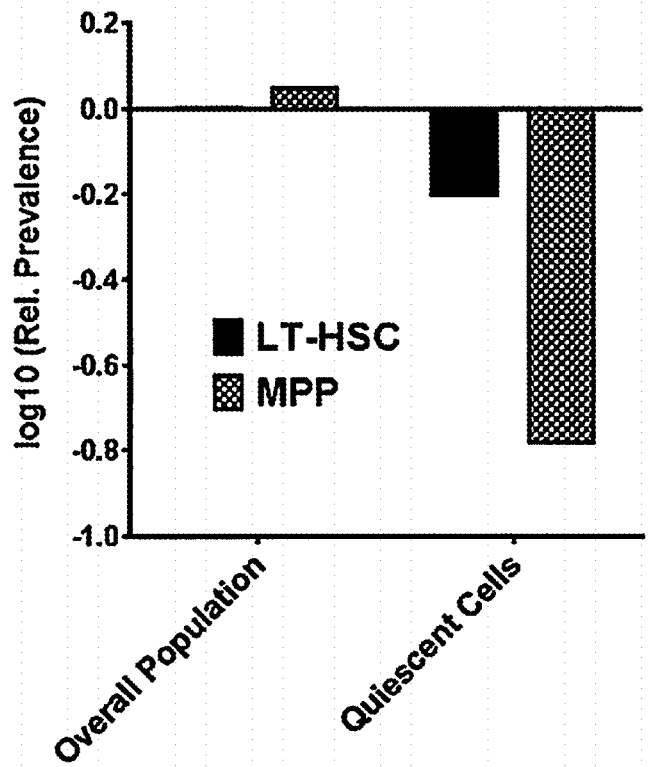
FIG. 8 shows that Gdf1 treatment promotes quiescence exit of hematopoietic progenitor cells.

Gdf1 treatment promotes quiescence exit of hematopoietic progenitor cells. Bone marrow of hybrid mice was treated with human recombinant Gdf1 at a concentration of 50 ng/mL for 24 hours. Flow cytometry was used in immunophenotyping cells into subpopulations of long-term hematopoietic stem cells (LT-HSC) and multipotent progenitor cells (MPP). LT-HSCs were defined as Lin–, C-kit+, Sca-1+, CD150+, CD48–. MPPs were defined as Lin–, C-kit+, Sca-1+, CD150–, CD48–. Quiescent cells were defined as CD34+. As shown in FIG. 8, addition of Gdf1 led to an increase in the population of MPPs in the overall pool of analyzed cells. Surprisingly, Gdf1 also led to a decrease in cells bearing the CD34 marker, indicating exit from quiescence in both the LT-HSC and MPP populations.

Figure 9:
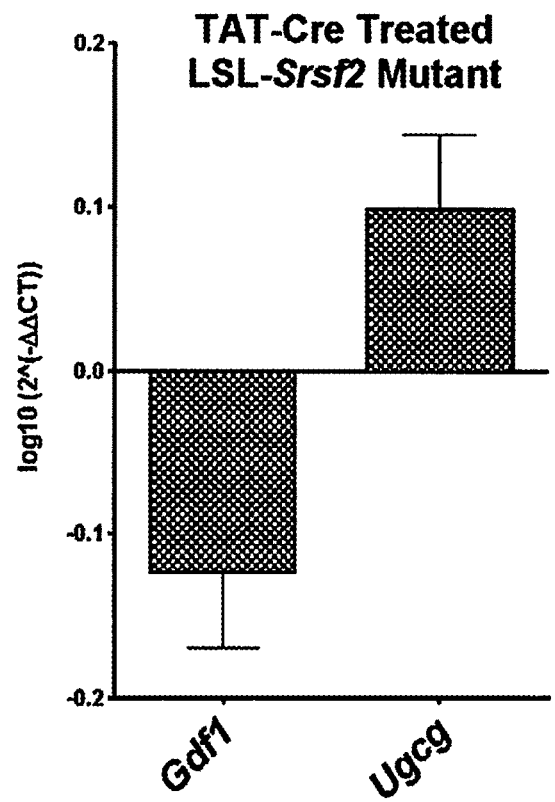
FIG. 9 shows srsf2 mutation recapitulates the inverse relationship between gdf1 and ugcg.

Srsf2 mutation recapitulates the inverse relationship between Gdf1 and Ugcg. Splenocytes of transgenic mice with inducible srsf2 mutation were treated with TAT-Cre recombinase at a concentration of 44 µM for 24 hours. Results were generated via qRT-PCR and normalized to housekeeping genes (Actb, RpII,Tbp). As shown in FIG. 9, expression of the srsf2 mutant gene led to a downregulation of gdf1 and an inverse upregulation of ugcg. These results mimic those generated by addition of hypomethylating agent, decitabine, indicating a potential link between splicing dysregulation, epigenetic control, and ceramide metabolism.

This study used splenocytes harvested from the respective mutant mice. Bone marrow was not studied because the TAT-Cre was toxic to them and so there could very well be major differences in bone marrow, which is the more interesting/relevant cell/tissue site (more below). This experiment was done in culture to introduce Cre (using the cell-penetrating TAT peptide).

We crossbred transgenic mice with a line that specifically expresses Cre of a cell-specific promoter (Mx1-Cre mice, which is also inducible). Mx1-Cre transgenic mice: B6.Cg-Tg(Mx1-cre)1Cgn/J (The Jackson Laboratory, Bar Harbor, Me. strain/003556).

The initial results with these Mx1-Cre x Srsf2 mutant mice show that there is differential expression between the spleen and bone marrow (opposite effects) (data not shown).

Figure 10:
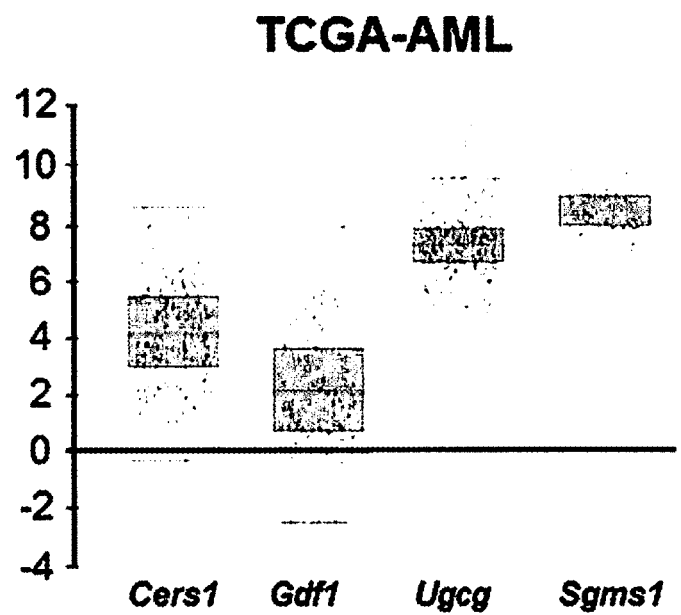
FIG. 10 shows that gdf1 is downregulated in AML cells compared to cers1, while pathways of ceramide neutralization are upregulated.

Gdf1 is downregulated in AML compared with cers1, while pathways of ceramide neutralization are upregulated. Adapted from The Cancer Genome Atlas. Tumors from patients with acute myeloid leukemia were sequenced and analyzed for expression of ceramide metabolic enzymes (n=200). As shown in FIG. 10, patients with AML showed a downregulation of gdf1 as compared to cers1 and an upregulation of ceramide neutralization pathways, via mediators ugcg and sgms1.

Figure 11:
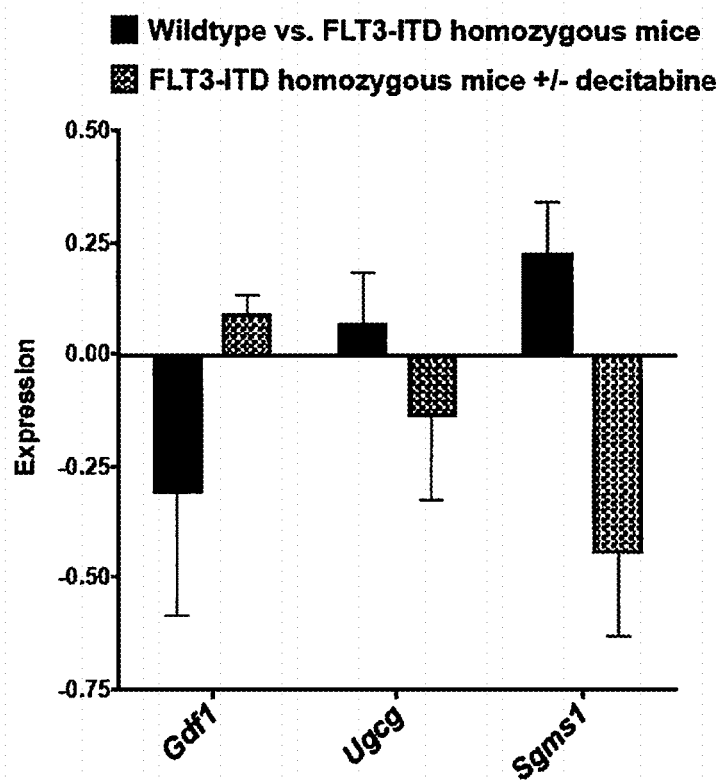
FIG. 11 shows that hypomethylating treatment reverses the effect of leukemogenic transgenes on ceramide detoxification.

Hypomethylating Treatment Reverses the Effect of Leukemogenic Transgenes on Ceramide Detoxification. Myeloid hematological malignancies such as AML and myelodysplastic syndrome (MDS) are frequently treated with hypomethylating agents such as decitabine. In particular, treatment and management of MDS commonly utilizes these strategies to attempt to prevent the transformation of this bone marrow failure-like condition to AML. In this experiment, we utilized aged FLT3$^{ITD}$ transgenic mice treated with/without decitabine and monitored the changes to the expression of genes in the bone marrow that regulate the production of bioactive sphingolipids. Intriguingly, an inverse relationship was observed between gdf1 and either ugcg (encodes glucosylceramide synthase (GCS) or sgms1 (encodes sphingomyelin synthase 1: SMGS1). See, FIG. 11 where the data of FIG. 6 is limited to gdf1, ugcg and sgms1.

Figure 12:
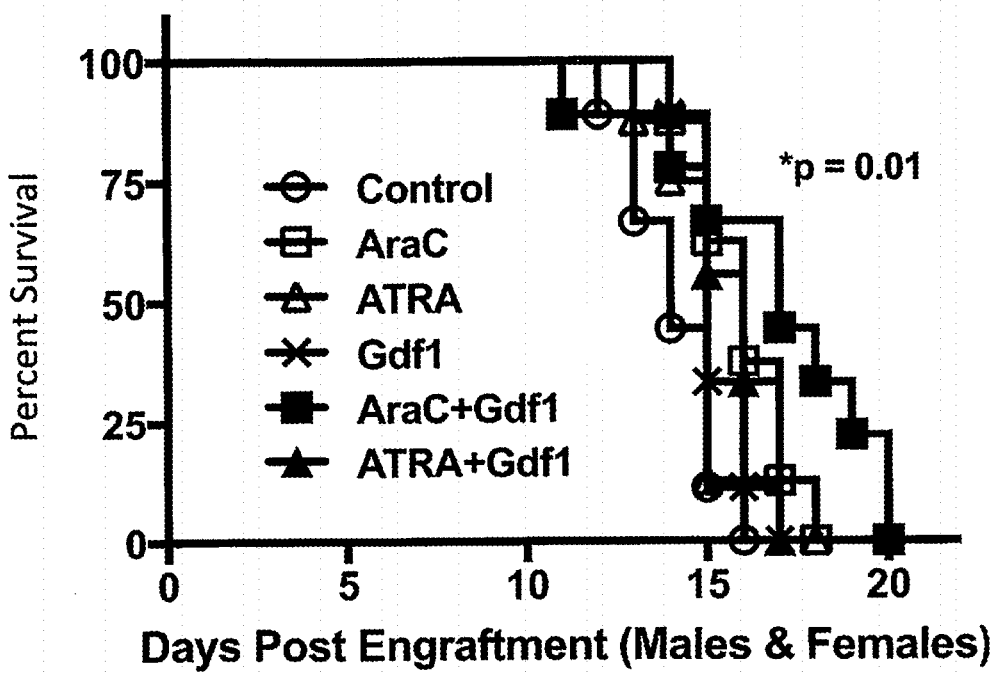
FIG. 12 shows recombinant gdf1 in combination with AraC extends the lifespan of C57BL/6J mice engrafted with C1498 AML cells.

Recombinant Gdf1 in Combination with AraC Extends the Lifespan of C57BL/6J Mice Engrafted with C1498 AML Cells. Cytarabine, also known as cytosine arabinoside (AraC). Briefly: C57BL/6J mice were engrafted with 2.5× 106 C1498 AML cells via tail vein injection. One week following engraftment, treatments were administered by intraperitoneal injection 3× per week for the duration of the trial and mouse survival (as determined by moribund status) was monitored (ATRA=all trans retinoic acid; AraC=cytarabine). See, FIG. 12.

We claim:

1. A method of treating a disorder in a subject, the method comprising: administering to a subject in need of such treatment, an effective amount of a composition comprising a recombinant Growth Differentiation Factor 1 (GDF1) protein set forth as:
  (i) SEQ ID NO: 1;
  (ii) an amino acid sequence having at least 95% sequence identity to SEQ ID NO: 1;
  (iii) SEQ ID NO: 2; or
  (iv) an amino acid sequence having at least 95% sequence identity to SEQ ID NO: 2;
  wherein the administration reduces ceramide neutralization in the subject, and wherein the disorder is a leukemia, a myelodysplastic syndrome (MDS), a hematopoietic malignancy, acute myeloid leukemia (AML), or a non-Hodgkin lymphoma.

2. The method of claim 1, further comprising detecting ceramide neutralization in the subject and comparing the ceramide neutralization detected in the subject to a control value, wherein the control value is the subject's ceramide neutralization measured at one or more of before, during, and after the administration of the composition, and further administering the composition to the subject until down-regulation of ceramide neutralization is detected.

3. The method of claim 2, wherein detecting ceramide neutralization comprises detecting one or both of the activity and the expression level of at least one ceramide metabolic enzyme.

4. The method of claim 2, wherein detecting ceramide neutralization comprises detecting a ceramide level or a ceramide metabolite level in a sample obtained from the subject.

5. The method of claim 1, wherein the ceramide neutralization occurs in a cell in the subject, and the cell is a neoplastic cell, a cancer cell, a leukemia cell, a hematopoietic stem cell, a splenocyte, a bone marrow cell, a leukemia stem cell, a cancer stem cell, a hematopoietic progenitor cell, an AML cell, a differentiated hematopoietic stem cell, a malignant hematopoietic cell, a lymphoid progenitor cell, or a myeloid progenitor cell.

6. The method of claim 5, wherein the cell is one or more of a pre-neoplastic, a pre-cancerous, and a pre-leukemic cell.

7. The method of claim 1, wherein the administration of the composition promotes differentiation of hematopoietic stem cells in the subject.

8. The method of claim 1, wherein the composition comprises the recombinant GDF1 protein set forth as SEQ ID NO: 1.

9. The method of claim 1, wherein the composition comprises the recombinant GDF1 protein set forth as SEQ ID NO: 2.

10. The method of claim 1, wherein the recombinant GDF1 protein is part of a fusion protein.

11. The method of claim 1, further comprising administering to the subject an effective amount of an additional agent capable of modulating at least one of GDF1 protein expression and activity, wherein the additional agent is a hypomethylating agent.

12. The method of claim 11, wherein the hypomethylating agent is decitabine (5-aza-2'-deoxycytidine).

13. The method of claim 1, further comprising administering to the subject an additional agent comprising cytosine arabinoside (AraC).

14. The method of claim 1, further comprising administering to the subject an additional agent comprising a ceramide compound.

15. The method of claim 14, wherein the administered ceramide compound comprises a nanoliposome.

* * * * *